(12) United States Patent
Santos et al.

(10) Patent No.: US 11,458,199 B2
(45) Date of Patent: Oct. 4, 2022

(54) LIPOSOME FORMULATIONS

(71) Applicant: OPKO Pharmaceuticals, LLC, Miami, FL (US)

(72) Inventors: Arturo Santos, Zapopan (MX); Phillip Frost, Miami Beach, FL (US); Jane Hsiao, Miami, FL (US)

(73) Assignee: OPKO Pharmaceuticals, LLC, Miami, FL (US)

( * ) Notice: Subject to any disclaimer, the term of this patent is extended or adjusted under 35 U.S.C. 154(b) by 0 days.

(21) Appl. No.: 16/426,712

(22) Filed: May 30, 2019

(65) Prior Publication Data

US 2019/0321467 A1    Oct. 24, 2019

Related U.S. Application Data

(63) Continuation-in-part of application No. 14/422,587, filed as application No. PCT/US2013/055084 on Aug. 15, 2013, now Pat. No. 10,548,841.
(Continued)

(51) Int. Cl.
*A61K 39/395* (2006.01)
*A61K 9/127* (2006.01)
(Continued)

(52) U.S. Cl.
CPC ........ *A61K 39/3955* (2013.01); *A61K 9/0014* (2013.01); *A61K 9/0019* (2013.01);
(Continued)

(58) Field of Classification Search
CPC .............. A61K 39/3955; A61K 9/0014; A61K 9/0019; A61K 9/0048; A61K 9/1271;
(Continued)

(56) References Cited

U.S. PATENT DOCUMENTS 5,714,163 A * 2/1998 Forssen .................. A61K 9/127
424/450
6,565,861 B1   5/2003  Tiffany et al.
(Continued)

FOREIGN PATENT DOCUMENTS

WO    2007076274 A2    7/2007

OTHER PUBLICATIONS

Peer et al, Nature Nanotechnology, 2, 2007, 751 (Year: 2007).*
(Continued)

*Primary Examiner* — Gollamudi S Kishore
(74) *Attorney, Agent, or Firm* — OPKO Pharmaceuticals, LLC; Monte R. Browder

(57) ABSTRACT

The present invention relates to pharmaceutical formulations comprising an anti angiogenic compound such as a monoclonal antibody or fragment thereof selected from, for example, ranibizumab, which is a vascular endothelial growth factor binder which inhibits the action of VEGF, and a delivery agent selected from a pharmaceutically acceptable liposome. The formulations are useful in the treatment of a variety of angiogenic disorders and diseases in animals and people, and, preferably, in ophthalmic disorders selected from age-related macular degeneration, diabetic macular edema and corneal neovascularization.

8 Claims, 9 Drawing Sheets

Results: Central Foveal Thickness-Contra-lateral eyes

Related U.S. Application Data

(60) Provisional application No. 62/848,907, filed on May 16, 2019, provisional application No. 61/862,300, filed on Aug. 5, 2013, provisional application No. 61/791,693, filed on Mar. 15, 2013, provisional application No. 61/691,455, filed on Aug. 21, 2012.

(51) Int. Cl.
    *A61K 9/00* (2006.01)
    *A61K 31/58* (2006.01)
    *A61P 27/02* (2006.01)
    *A61K 31/4045* (2006.01)
    *A61K 39/00* (2006.01)

(52) U.S. Cl.
    CPC .......... *A61K 9/0048* (2013.01); *A61K 9/1271* (2013.01); *A61K 31/4045* (2013.01); *A61K 31/58* (2013.01); *A61P 27/02* (2018.01); *A61K 2039/505* (2013.01); *A61K 2039/55555* (2013.01)

(58) Field of Classification Search
    CPC ................. A61K 31/4045; A61K 31/58; A61K 2039/505; A61K 2039/55555; A61K 9/10; A61K 47/14; A61K 2039/54; A61P 27/02; C07K 16/22
    See application file for complete search history.

(56) References Cited

U.S. PATENT DOCUMENTS

| | | | |
|---|---|---|---|
| 6,610,322 B1 | 8/2003 | Keller et al. | |
| 6,958,160 B1 | 10/2005 | Keller et al. | |
| 7,718,190 B2* | 5/2010 | Keller | A61K 9/1271 424/450 |
| 2004/0013693 A1* | 1/2004 | Bobotas | A61K 9/0095 424/400 |
| 2004/0071761 A1 | 4/2004 | Miller et al. | |
| 2005/0202034 A1* | 9/2005 | Rasmussen | A61P 17/00 424/185.1 |
| 2005/0287180 A1* | 12/2005 | Chen | A61K 47/24 514/4.8 |
| 2006/0165744 A1 | 7/2006 | Jamil et al. | |
| 2007/0026061 A1* | 2/2007 | Ali | A61K 9/127 424/450 |
| 2007/0148225 A1 | 6/2007 | Weiner et al. | |
| 2010/0111963 A1* | 5/2010 | Shams | C07K 16/22 424/145.1 |
| 2011/0009374 A1* | 1/2011 | Keller | A61P 43/00 514/177 |
| 2011/0033468 A1 | 2/2011 | Shih et al. | |
| 2011/0033527 A1 | 2/2011 | Wu et al. | |
| 2011/0040113 A1 | 2/2011 | Wu et al. | |
| 2011/0097340 A1 | 4/2011 | Ramachandra et al. | |
| 2011/0230476 A1 | 9/2011 | Niu et al. | |
| 2012/0009185 A1 | 1/2012 | Shams | |

OTHER PUBLICATIONS

Abell, R., et al., "Anterior Chamber Flare After Femtosecond Laser-Assisted Cataract Surgery", Journal of Cataract & Refractive Surgery, vol. 39, No. 9, pp. 1321-1326, (2013). Abstract.

Ah-Fat, F., et al., "Vitreous Loss During Conversion from Conventional Extracapsular Cataract Extraction to Phacoemulsification", Journal of Cataract & Refractive Surgery, vol. 24, No. 6, pp. 801-805, (1998). Abstract.

Allen, T., et al., "Drug Delivery Systems: Entering the Mainstream", Science, vol. 303, pp. 1818-1822, (2004). Abstract.

Altamirano-Vallejo, J., et al., "Characterization and Pharmacokinetics of Triamcinolone Acetonide-Loaded Liposomes Topical Formulations for Vitreoretinal Drug Delivery", Journal of Ocular Pharmacology and Therapeutics, vol. 34, pp. 416-425, (2018).

Araujo, J., et al., "Release Profile and Transscleral Permeation of Triamcinolone Acetonide Loaded Nanostructed Lipid Carriers (TA-NLC): In Vitro and Ex Vivo Studies", Nanomedicine, vol. 8, No. 6, pp. 1034-1041. (2011).

Arikan, G., et al., "Immediate Intraocular Pressure Rise After Intravitreal Injection of Ranibizumab and Two Doses of Triamcinolone Acetonide", International Journal of Ophthalmology, vol. 4, No. 4, pp. 402-405, (2011).

Baartman, B., et al., "Prednisolone Versus Dexamethasone for Prevention of Pseudophakic Cystoid Macular Edema", Canadian Journal of Ophthalmology, vol. 53, No. 2, pp. 131-134, (2018). Abstract.

Bangham, A., et al., "Negative Staining of Phospholipids and Their Structural Modification by Surface-Active Agents as Observed in the Electron Microscope", Journal of Molecular Biology, vol. 8, pp. 660-668, (1964).

Becerra, E., et al., "Clinical Evidence of Intravitreal Triamcinolone Acetonide in the Management of Age-Related Macular Degeneration", Current Drug Targets, vol. 12, No. 2, pp. 149-172, (2011). Abstract.

Belair, M., et al., "Incidence of Cystoid Macular Edema After Cataract Surgery in Patients With and Without Uveitis Using Optical Coherence Tomography", American Journal of Ophthalmology, vol. 148, No. 1, pp. 128-135, (2009). Abstract.

Bhagat, N., et al., "Diabetic Macular Edema: Pathogenesis and Treatment", Survey of Ophthalmology, vol. 54, No. 1, pp. 1-32, (2009). Abstract.

Bochot, A., et al., "Liposomes for Intrevitreal Drug Delivery: A State of the Art", Journal of Controlled Release, vol. 161, pp. 628-634, (2012).

Campochiaro, P., et al., "Ranibizumab for Macular Edema Due to Retinal Vein Occlusions: Implication of VEGF as a Critical Stimulator", Molecular Therapy, vol. 16, No. 4, pp. 791-799, (2008).

Chan, CK., et al., "Ocular-Hypertensive Response and Corneal Endothelial Changes After Intravitreal Triamcinolone Injections in Chinese Subjects: A 6-Months Follow-Up Study". Eye, vol. 19, pp. 625-630, (2005).

Chen, Y., et al., "Selection and Analysis of an Optimized Anti-VEGF antibody: crystal structure of an Affinity-matured Fab in Complex with Antigen", Journal of Molecular Biology, vol. 293, No. 4, pp. 865-881, (1999). Abstract.

Chinchurreta, A., et al., "Comparative Study of the Efficacy and Safety of Bromfenac, Nepafenac and Diclofenac Sodium for the Prevention of Cystoid Macular Edema after Phacoemulsification", International Journal of Ophthalmology, vol. 11, No. 7, pp. 1210-1216, (2018). Abstract.

Chu, C., et al., "Risk Factors and Incidence of Macular Edema after Cataract Surgery: A Database Study of 81 984 Eyes", American Academy of Ophthalmology, vol. 123, No. 2, pp. 316-323, (2016).

Chu, YK., et al., "Objective Evaluation of Cataract Progression Associated with a High Dose Intravitreal Triamcinolone Injection", Eye, vol. 22, pp. 895-899, (2008).

Coscas, G., et al., "Macular Edema: Definition and Basic Concepts", Developments in Ophthalmology, vol. 58, pp. 1-10, (2017). Abstract.

Cugati, S., et al., "Ten-Year Incidence of Retinal Vein Occlusion in an Older Population", The Archives of Ophthalmology, vol. 124, pp. 726-732, (2006).

Di Tommaso, C., et al., "Novel Micelle Carriers for Cyclosporin A Topical Ocular Delivery: In Vivo Cornea Penetration, Ocular Distribution and Efficacy Studies", European Journal of Pharmaceutics and Biopharmaceutics, vol. 81, No. 2, pp. 257-264, (2012). Abstract.

Ebrahem, Q., et al., "Triamcinolone Acetonide Inhibits IL-6-and VEGF-Induced Angiogenesis Downstream of the IL-6 and VEGF Receptors", Investigative Ophthalmology & Vision Science, vol. 47, No. 11, pp. 4935-4941, (2008).

Ecsedy, M., et al., "Effect of Femtosecond Laser Cataract Surgery on the Macula", Journal of Refractive Surgery, vol. 27, No. 10, pp. 717-722, (2011). Abstract.

(56) References Cited

OTHER PUBLICATIONS

El, G., et al., "Efficacy of Addition of Nepafenac 0.1% to Steroid Eye Drops in Prevention of Post-Phaco Macular Edema in High-Risk Eyes", European Journal of Ophthalmology, 1120672118799626, (2008). Abstract.
Ewe, S., et al., "Cystoid Macular Edema After Femtosecond Laser-Assisted Versus Phacoemulsification Cataract Surgery", Journal of Cataract & Refractive Surgery, vol. 41, No. 11, pp. 2373-2378, (2015). Abstract.
Feigenbaum, A., et al., "Intravitreal Injection of Penicillin in a Case of Incipient Abcess of the Vitreous Following Extracapsular Cataract Extraction; Perfect Cure", Ophthalmologica, vol. 110, pp. 300-305, (1945).
Fong, D., et al., "Retinopathy in Diabetes" Diabetes Care, vol. 27, No. 1, pp. s84-s87, (2004).
Gaudana, R., et al., "Ocular Drug Delivery", The AAPS Journal, vol. 12, No. 3, pp. 348-360, (2010).
Gaudana, R., et al., "Recent Perspective in Ocular Drug Delivery", Pharmaceutical Research, vol. 26, No. 5, pp. 1197-1216, (2009).
Gonzalez-De La Rosa, A., et al., "Novel Triamcinolone Acetonide-Loaded Liposomes Topical Formulation for the Treatment of Cystoid Macular Edema After Cataract Surgery: A Pilot Study", Journal of Ocular Pharmacology and Therapeutics, vol. 35, No. 2, pp. 106-115, (2019).
Guo, S., et al., "Management of Pseudophakic Cystoid Macular Edema", Survey of Ophthalmology, vol. 60, No. 2, pp. 123-137, (2015). Abstract.
Habot-Wilner, Z., et al., "Intravitreal Triamcinolone Acetonide as Adjunctive Treatment with Systemic Therapy for Uveitic Macular Edema", European Journal of Ophthalmology, vol. 21, Suppl 6, pp. S56-S61, (2011).
Haller J. et al., "Randomized, Sham-Controlled Trial of Dexamethasone Intravitreal Implant in Patients with Macular Edema Due to Retinal Vein Occlusion", Ophthalmology, vol. 117, pp. 1134-1146, (2010).
Hathout, R., et al., "Liposomes as an Ocular Delivery System for Acetazolamide: In Vitro and in Vivo Studies", AAPS PharmSciTech, vol. 8, No. 1, pp. E1-E12, (2007). Abstract.
Henderson, B., et al., "Clinical Pseudophakic Cystoid Macular Edema. Risk Factors for Development and Duration After Treatment", Journal of Cataract & Refractive Surgery, vol. 33, No. 9, pp. 1550-1558, (2007). Abstract.
Janssen, A., et al., "Peptide-Targeted Peg-Liposomes In Anti-Angiogenic Therapy", International Journal of Pharmaceutics, vol. 254, pp. 55 58, (2003).
Jonas, J., et al., "Branch Retinal Vein Occlusion Treated by Intravitreal Triamcinolone Acetonide", Eye, vol. 19, pp. 65-71,(2005).
Kim, J., et al., "A Prospective, Randomized, Dose-Escalation Intravitreal Steroid Injection Study for Refractory Diabetic Macular Edema" Retina, vol. 28, pp. 735-740, (2008).
Klibanov A., et al., "Amphipathic Polyethyleneglycols Effectively Prolong the Circulation Time of Liposomes", FE, vol. 268, No. 1, pp. 235-237, (1990).
Kwon, S., et al., "Comparison of Natural Course, Intravitreal Triamcinolone, and Intravitreal Bevacizumab for Treatment of Macular Edema Secondary to Branch Retinal Vein Occlusion", Journal of Ocular Pharmacology and Therapeutics, vol. 29, No. 1, pp. 5-9, (2013).
Lam, D., et al., "Intravitreal Triamcinolone for Diabetic Macular Oedema in Chinese Patients: Six-Month Prospective Longitudinal Pilot Study", Clinical Exp Ophthalmology, vol. 32, pp. 562-572, (2004).
Lee, H., et al., "Intravitreal Triamcinolone as Primary Treatment of Cystoid Macular Edema Secondary to Branch Retinal Vein Occlusion", Retina, vol. 25, pp. 551-555, (2005).
Lee, S., et al., "Evaluation of Clearance Mechanisms with Transscleral Drug Delivery", Investigative Ophthalmology & Visual Science, vol. 52, No. 10, pp. 5205-5212, (2010).
Lee, V., et al., "Ocular Drug Bioavailability From Topically Applied Liposomes", Survey of Ophthalmology, vol. 29, No. 5, pp. 335-348, (1985).

Liu, H., et al., "A Lipid Nanoparticle System Improves sIRNA Efficacy in RPE Cells and a Laser-Induced Murine CNV Model", Investigative Ophthalmology & Visual Science, vol. 52, No. 7, pp. 4789-4794, (2011).34-1041, (2011).
Lopez-Berestein, G., et al., "Effects of Sterols on the Therapeutic Efficacy of Liposomal Amphotericin B in Murine Candidiasis", Cancer Drug Delivery, vol. 1, No. 1, pp. 37-42, (1983).
Mansoor, S.,et al., "Intraocular Sustained-Release Delivery Systems for Triamcinolone Acetonide", Pharmaceutical Research, vol. 26, No. 4, pp. 770-784, (2009).
McAllister I., et al., "Effect of Triamcinolone Acetonide on Vascular Endothelial Growth Factor and Occludin Levels in Branch Retinal Vein", The American Journal of Ophthalmology, vol. 147, pp. 838-846, (2009).
Meyer, C., et al., "Current Treatment Approaches in Diabetic Macular Edema", Ophthalmologica, vol. 221, No. 2, pp. 118-131, (2007). Abstract.
Moshfeghi, D., et al., "Acute Endophthalmitis Following Intravitreal Triamcinolone Acetonide Injection", American Journal of Ophthomology, vol. 103, pp. 791-796, (2003).
Nagy, Z., et al., "Macular Morphology Assessed by Optical Coherence Tomography Image Segmentation After Femtosecond Laser-Assisted and Standard Cataract Surgery", Journal of Cataract & Refractive Surgery, vol. 38, No. 6, pp. 941-946, (2012). Abstract.
Nikica, G., et al., "Cystoid Macular Edema in Anterior Chamber Lens Implantation Following Posterior Capsule Rupture", Documenta Ophthalmologica, vol. 81, No. 3, pp. 309-315, (1992). Abstract.
Nishimura, E., "Drug Treatment for Diabetic Retinopathy: Current and Future", Journal of The Showa University Society, vol. 70, No. 1, pp. 45-51, (2010). Abstract.
Noma, H., et al., "Pathogenesis of Macular Edema with Branch Retinal Vein Occlusion and Intraocular Levels of Vascular Endothelial Growth Factor and Interleukin-6", American Journal of Opthalmology, vol. 140, pp. 256-261, (2005).
Oku, N., "Selective Release of Non-Electrolytes from Liposomes Upon Perturbation of Bilayers by Temperature Change of Polyene Antibiotics", Biochimica et Biophysica Acta, vol. 595, pp. 277-290, (1980).
Panteleontidis, V., et al., "Latanoprost-Dependent Cystoid Macular Edema Following Uncomplicated Cataract Surgery in Pseudoexfoliative Eyes", Ophthalmic Surgery, Lasers and Imaging Retina, vol. 9, pp. 1-5, (2010). Abstract.
Park, S., et al., "Aqueous Vascular Endothelial Growth Factor Levels are Associated With Serous Macular Detachment Secondary to Branch Retinal Vein Occlusion", The Journal of Retinal and Vitreous Disease, vol. 30, No. 2, pp. 281-286, (2010).
Perente, I., et al., "Evaluation of Macular Changes After Uncomplicated Phacoemulsification Surgery by Optical Coherence Tomography", Current Eye Research, vol. 32, No. 3, pp. 241-247, (2007). Abstract.
Presta, L., et al., "Humanization of an Anti-Vascular Endothelial Growth Factor Monoclonal Antibody for the Therapy of Solid Tumors and Other Disorders", Cancer Research, vol. 57, pp. 4593-4599, (1997).
Purslow, C., et al., "Ocular Surface Temperature: A Review", Eye Contact Lens, vol. 31, No. 3, pp. 117-123, (2005). Abstract.
Rogers, S., et al., "The Prevalence of Retinal Vein Occlusion: Pooled Data From Population Studies from the United States, Europe, Asia, and Australia" Ophthalmology, vol. 117, No. 2, pp. 313-319, (2010).
Roskoski, R., et al., "Sunitinib: A VEGF and PDGF Receptor Protein Kinase and Angiogenesis Inhibtor" Biochemical and Biophysical Research Communications, vol. 356, No. 2, pp. 323-328, (2007). Abstract.
Rossetti, L., et al., "Cystoid Macular Edema Following Cataract Surgery", Current Opinion in Ophthalmology, vol. 11, No. 1, pp. 65-72, (2000), Abstract.
Rui, A., "Retina", Tianjin Science and Technology Translation and Publishing Company, pp. 2235-2236, (2011).
Schmier, J., et al., "Evaluation of Costs for Cystoid Macular Edema Among Patients After Cataract Surgery", Retina, vol. 27, No. 5, pp. 621-628, (2007). Abstract.

(56) References Cited

OTHER PUBLICATIONS

Scott, I, et al., "A Randomized Trial Comparing the Efficacy and Safety of Intravitreal Triamcinolone with Standard Care to Treat Vision Loss Associated with Macular Edema Secondary to Branch Retinal Vein Occlusion: The Standard Care vs Corticosteroid for Retinal Vein Occlusion (SCORE) Study Report 6". The Archives of Ophthalmology, vol. 127, pp. 1115-1128, (2009).
Shabir, G., et al., "Validation of High-Performance Liquid Chromatography Methods for Pharmaceutical Analysis: Understanding the Differences and Similarities Between Validation Requirements of the US Food and Drug Administration, the US Pharmacopeia and the International Conference on Harmonization", Journal of Chromatography A, vol. 987, No. 1-2, pp. 57-66, (2003). Abstract.
Shimazaki, H., et al, "Edaravone-Loaded Liposome Edyedrops Protects Against Light-Induced Retinal Damage in Mice", Investigative Ophthalmology & Visual Science, vol. 52, No. 10, pp. 7289-7297, (2011).
Shubber, S., et al., "Mechanism of Mucosal Permeability Enhancement of CriticalSorb (R) (Solutol(R) HS15) Investigated in Vitro in Cell Cultures", Pharmaceutical Research, vol. 32, pp. 516-527, (2015).
Singh, K., et al., "Liposomal Ophthalmic Drug Delivery system I. Triamcinolone Acetonide", International Journal of Pharmaceutics, vol. 16, No. 3, pp. 339-344, (1983). Abstract.
Smithen, L., "Intravitreal Triamcinolone Acetonide and Intraocular Pressure",The American Journal of Ophthalmology, vol. 138, 740-743, (2004).
Suzuki, Y., et al., "Retinoic Acid Controls Blood Vessel Formation by Modulating Endothelial and Mural Cell Interaction Via Suppression of Tie2 Signaling in Vascular Progenitor Cells", Blood, vol. 104, No. 1, pp. 166-169, (2004).
Ty, R., et al., "Comparison of Clinical Outcomes Between Femtosecond Laser-Assisted Versus Conventional Phacoemulsification", Eye and Vision, vol. 5, No. 8, pp. 1-29, (2018).
Van Rooijen, N., et al., "Liposomes in Immunology: Multilamellar Phosphatidylcholine Liposomes as a Simple, Biodegradable and Harmless Adjuvant Without Any Immunologenic acitivity of its Own", Immunological Communications, vol. 9, No. 3, pp. 243-256, (1980).
Veritti, D., et al., "Drug Safety Evaluation of Intravitreal Triamcinolone Acetonide", Expert Opinion Drug Safety, vol. 11, pp. 331-340, (2012).
Wingate, R., "Intravitreal Triamcinolone and Elevated Intraocular Pressure", Ophthalmology, vol. 27, pp. 431-432, (1999).
Yeh, P., et al., "Latanoprost and Clinically Significant Cystoid Macular Edema after Uneventful Phacoemulsification with Intraocular Lens Implantation", Journal of Cataract & Refractive Surgery, vol. 28, No. 10, pp. 1814-1818, (2002). Abstract.
Yilmaz, T., et al., "Triamcinolone and Intraocular Sustained-Release Delivery Systems in Diabetic Retinopathy", Current Pharmaceutical Biotechnology, vol. 12, No. 3, pp. 337-346, (2011).
Ylinen, P., et al., "Anti-inflammatory Medication Following Cataract Surgery: a Randomized Trial Between Preservative-Free Dexamethasone, Diclofenac and Their Combination", Acta Ophthalmologica, vol. 96, No. 5, pp. 486-493, (2018). Abstract.
Young, S., et al., "Safety and Efficacy of Intravitreal Triamcinolone for Cystoid Macular Oedema in Uveitis", Clinical Experimental and Ophthalmology, vol. 29, pp. 2-6, (2001).
Zhang X., et al., "Glucocorticoids: Structure, Signaling and Molecular Mechanisms in the Treatment of Diabetic Retinopathy and Diabetic Macular Edema", Current Molecular Medicine, vol. 14, No. 3, pp. 376-384, (2014).
Zur, D., et al., "Postsurgical Cystoid Macular Edema", Developments in Ophthalmology, vol. 58, pp. 178-190, (2017). Abstract.
"Photocoagulation for Diabetic Macular Edema. Early Treatment Diabetic Retinopathy Study Report No. 1. Early Treatment Diabetic Retinopathy Study Research Group", JAMA Ophthalmology (formerly Archives of Ophthalmology), vol. 103, No. 12, pp. 1796-1806, (1985).
Genentech official Lucientis® website, https://www.lucentis.com/wet-amd/patient-information/why-lucentis.html.
Brown, D., et al., "Ranibizumab Versus Verteporfin for Neovascular Age-Related Macular Degeneration", The New England Journal of Medicine, vol. 355, No. 14, pp. 1432-1444, (2006).
Rosenfeld, P., et al., "Ranibizumab for Neovascular Age-Related Macular Degeneration", New England Journal of Medicine, vol. 355, No. 14, pp. 1419-1431, (2006).
Mitchell, P., et al., "Ranibizumab (Lucentis) in Neovascular Age-Related Macular Degeneration: Evidence From Clinical Trials", British Journal of Ophthalmology, vol. 94, No. 1, pp. 2-13, (2010).
Meyer, C., et al., "Incidence of Rhegmatogenous Retinal Detachments After Intravitreal Antivascular Endothelial Factor Injections", Acta Ophthalmologica, vol. 89, pp. 70-75, (2011).
Lyall, D., et al., "Postintravitreal Anti-VEGF Endophthalmitis in the United Kingdom: Incidence, Features, Risk Factors, and Outcomes", Eye, vol. 26, pp. 1517-1526, (2016).
Abdelfattah, N., et al., "S. Progression of Macular Atrophy in Patients with Neovascular Age-Related Macular Degeneration Undergoing Antivascular Endothelial Growth Factor Therapy", Retina, vol. 36, No. 10, pp. 1843-1850, (2016).
Munk, M., et al., "Macular Atrophy in Patients with Long-Term Anti-VEGF Treatment for Neovascular Age-Related Macular Degeneration", Acta Ophthalmologica, vol. 94, No. 8, pp. e757-e764, (2016).
Porta M., et al., "Intravitreal Anti-VEGF Agents and Cardiovascular Risk",. Internal and Emergency Medicine, vol. 15, No. 2, pp. 199-210, (2020).
Bandello, F., et al., "Diabetic Retinopathy, Diabetic Macular Edema, and Cardiovascular Risk: The Importance of a Long-Term Perspective and Multidisciplinary Approach to Optimal Intravitreal therapy" Acta Diabetologica , vol. 57, No. 5, pp. 513-526, (2020).
Jeon, H., et al., "Cardiovascular Risk in Patients Receiving Ranibizumab for Exudative Age-Related Macular Degeneration: A Nationwide Self-Controlled Case-Series Study", British Journal of Ophthalmology vol. 10; bjophthalmol-2020-316373. doi: 10.1136/bjophthalmol-2020-316373.
Gillies, M., et al., "Macular Atrophy in Neovascular Age-Related Macular Degeneration: A Randomized Clinical Trial Comparing Ranibizumab and Aflibercept (RIVAL Study)", American Academy of Ophthalmology, vol. 127. No. 2, pp. 198-210, (2020).
Sadda, S., et al., "Macular Atrophy in the HARBOR Study for Neovascular Age-Related Macular Degeneration", American Academy of Ophthalmology, vol. 125, No. 6, pp. 878-886, (2018).
Stewart , M., "Extended Release Anti-VEGF Systems: A Strategy Whose Time Has Come? Or Already Gone? Experiment", Review of Ophthalmology, vol. 11, pp. 167-169, (2016).
Burgett, L., et al., "IOP and Anti-VEGF Drugs: What We Know So Far" Retina Specialist, vol. 11, pp. 1-10, (2019).
Azad, R., et al., "The Economic Implications of the Use of Anti-Vascular Endothelial Growth Factor Drugs in Age-Related Macular Degeneration", Indian Journal of Ophthalmology, vol. 55, No. 6, pp. 441-443, (2007).
Santos, A., et , "Breaking Down The Barrier: Topical Liposomes as Nanocarriers for Drug Delivery into de Posterior Segment of the Eyeball", Role of Novel Drug Delivery Vehicles in Nanobiomedicine. DOI: http://dx.doi.org/10.5772/intechopen.86601.
Yalcinbayir, O., et al., "Intravitreal Versus Sub-Tenon Posterior Triamcinolone Injection in Bilateral Diffuse Diabetic Macular Edema", Ophthalmologica, vol. 225, pp. 222-227, (2011).
Veritti, D., et al., "Drug Safety Evaluation of Intravitreal Triamcinolone Acetonide", Drug Safety Evaluation, vol. 11, No. 2, pp. 331-340, (2012).
Van Der Reis , M., et al., "A Systematic Review of the Adverse Events of Intravitreal Anti-Vascular Endothelial Growth Factor Injections", Retina, vol. 31., No. 8, pp. 1449-1469, (2011).
Kim, S., et al., "Transport Barriers in Transscleral Drug Delivery for Retinal Diseases", Ophthalmic Research, vol. 39, pp. 244-254, (2007).
Lee, S., et al., "Evaluation of Clearance Mechanisms with Transscleral Drug Delivery", Investigative Ophthalmology and Visual Science, vol. 51, No. 10, pp. 5205-5212, (2010).

(56) References Cited

OTHER PUBLICATIONS

Allen, T., et al., "Drug Delivery Systems: Entering The Mainstream", Science, vol. 303, pp. 1818-1822, (2004).
Bochot, A., et al., "Liposomes for Intravitreal Drug Delivery: A State of The Art", Journal of Control Release, vol. 161, pp. 628-634, (2012).
Klibanov, A., et al., "Amphipathic Polyethyleneglycols Effectively Prolong the Circulation Time of Liposomes",. FEBS Letters, vol. 268, No. 1, pp. 235-237, (1990).
Oku, N., et al., "Selective Release of Non-Electrolytes From Liposomes Upon Perturbation of Bilayers by Temperature Change or Polyene Antibiotics", Biochimica et Biophysica Acta, vol. 595, pp. 277-290, (1980).
Bangham, A., "Negative Staining of Phospholipids and Their Structural Modification by Surface-Active Agents as Observed in the Electron Microscope", Journal of Molecular Biology, vol. 8, pp. 660-668, (1964).
Oku, N., "Anticancer Therapy Using Glucuronate Modified Long-Circulating Liposomes", Advanced Drug Delivery Reviews, vol. 40, pp. 63-73, (1999).
Van Rooijen, N., et al., "Liposomes in Immunology: Multilamellar Phosphatidylcholine Liposomes as a Simple Biodegradable and Harmless Adjuvant Without Any Immunogenic Activity of its Own", Immunological Communication, vol. 9, No. 3, pp. 243-256, (1980).
Chen J., et al., "Potential Penetration of Topical Ranibizumab (Lucentis) in the Rabbit Eye", Eye, vol. 25, pp. 1504-1511, (2011).
Nguyen, Q., et al., "Ranibizumab for Diabetic Macular Edema. Results from 2 phase III Randomized Trials: RISE and RIDE", Ophthalmology, vol. 119, No. 4, pp. 789-799, (2012).
Altamirano-Vallejo J., et al., "Characterization and Pharmacokinetics of Triamcinolone Acetonide-Loaded Liposomes Topical Formulations for Vitreoretinal Drug Delivery", Journal of Ocular Pharmacology and Therapeutics, vol. 34, No. 5, pp. 416-425, (2018).
Navarro-Partida, J., et al., "Safety and Tolerability of Topical Ophthalmic Triamcinolone Acetonide-Loaded Liposomes Formulation and Evaluation of its Biologic Activity in Patients with Diabetic Macular Edema", Pharmaceutics, vol. 13, No. 322, pp. 1-17, (2021).
Navarro-Partida, J., et al., "Topical Triamcinolone Acetonide-Loaded Liposomes as Primary Therapy for Macular Edema Secondary to Branch Retinal Vein Occlusion: A Pilot Study," Journal of Ocular Pharmacology and Therapeutics, vol. 36, No. 6, pp. 1-11, (2020).
Gonzalez-De la Rosa, A., et al., "A Novel Triamcinolone Acetonide-Loaded Liposomal Topical Formulation Improves Contrast Sensitivity Outcome After Femtosecond Laser-Assisted Cataract Surgery", Journal of Ocular Pharmacology and Therapeutics, vol. 35, vol. 9, pp. 512-521, (2019).
Gonzalez-De la Rosa, A., et al., "Triamcinolone Acetonide-Loaded Liposomes Topical Formulation for the Treatment of Cystoid Macular Edema After Cataract Surgery: A Pilot Study", Journal of Ocular Pharmacology and Therapeutics, vol. 35, No. 2, pp. 106-115, (2019).
Meza-Rios, A., et al., "Therapies Based on Nanopartictes for Eye Drug Delivery". Ophthalmology Therapy, vol. 9, No. 3, pp. 1-14, (2020).
Clinical Trials. Gov, Identifier, "NCT01112085".
Navarro-Partida J., et al., "Lipid-Based Nanocarriers as Topical Drug Delivery Systems for Intraocular Diseases", Pharmaceutics, vol. 13, No. 5, pp. 1-25, (2021).
Schuerer, N., et al., "Implications for o\Ophthalmic Formulations: Ccular Buffers Show Varied Cytotoxic Impact on Human Corneal-Limbal and Human Conjunctival Epithelial Cells", Cornea, vol. 36, No. 6, pp. 712-718, (2017).
Sercombe, L, et al., "Advances and Challenges of Liposome Assisted Drug Delivery", Frontiers in Pharmacology, vol. 6, No. 286, pp. 1-13, (2015).
LUCENTIS® (ranibizumab injection), Intravitreal Injection; Initial U.S. Approval: 2006.

\* cited by examiner

Phase contrast optical microscopy of QuSomes: multilamellar vesicles (left) and large unilamellar vesicles (right), 10 minutes after addition of water.

Results: Central Foveal Thickness-Contra-lateral eyes

Results: BCVA-Study Eyes

Results: BCVA Contra-lateral eyes

LIPOSOME FORMULATIONS

This application is a continuation-in-part of U.S. application Ser. No. 14/422,587 filed Feb. 19, 2015, which is a national phase application of PCT/US2013/055084 filed on Aug. 15, 2013, which claims priority of U.S. Provisional Patent Application Nos. 61/862,300 filed on Aug. 5, 2013, 61/791,693 filed Mar. 15, 2013, and 61/691,455 filed Aug. 21, 2012 and this application claims priority to U.S. Provisional Application No. 62/848,907 filed May 16, 2019, which are all incorporated herein by reference in their entirety.

FIELD OF THE INVENTION

The present invention relates to pharmaceutical formulations comprising an ophthalmic medication typically applied by intravitreal injection to the eye and a liposomal delivery agent that permits topical application to the eye of said intravitreal medication. The present invention also relates to an anti-angiogenic compound such as a monoclonal antibody or fragment thereof selected from, for example, ranibizumab, which is a vascular endothelial growth factor binder which inhibits the action of VEGF, and/or a multi-kinase VEGFR and PDGFR inhibitor, for example, sunitinib, and a delivery agent selected from a pharmaceutically acceptable liposome. The formulations are useful in the treatment of a variety of angiogenic disorders and diseases in animals and people, and, preferably, in ophthalmic disorders selected from age-related macular degeneration, diabetic macular edema and corneal neovascularization.

BACKGROUND OF THE INVENTION

Ophthalmic disease treatment typically requires either topical administration or intravitreal injection of the particular drug to the eye depending upon the particular disease or condition and the effectiveness of the route of administration with respect to the particular drug and disease. In certain diseases or conditions of the eye effective treatment can only be achieved if the drug is administered by intravitreal injection. There are a litany of diseases and conditions of the eye that are effectively treated by intravitreal injection. At the same time, these injections can cause and/or are associated with serious side effects including eye infections (endophthalmitis), eye inflammation, retinal detachments and increases in eye pressure. Because of these side effects or risks topical treatment of the eye has been both the preferred route of administration of drugs to treat eye conditions and the Holy Grail because in almost all cases, topical administration of the drug does not effectively treat certain eye conditions, especially those conditions that occur in the back of the eye. Thus there is a need to develop formulations that effectively treat said conditions and that eliminate the need to have intravitreal injections. The present inventors believe they have found such a vehicle. U.S. Pat. No. 6,884,879 discloses various anti-VEGF antibodies. This patent specifically describes and claims the monoclonal antibody ranibizumab which is approved and marketed under the brand name LUCENTIS®. The antibodies disclosed therein are described as being capable of preventing, reversing and/or alleviating the symptoms of various diseases and are described as having the ability to inhibit VEGF-induced proliferation of endothelial cells and the ability to inhibit VEGF-induced angiogenesis. LUCENTIS® is approved for neovascular (wet) age-related macular degeneration (AMD) at a dosage strength of 0.5 mg (0.05 mL) by intravitreal injection one a month and, though less effective, the approved treatment may be administered to an injection every three months after an initial regimen of once a month for at least four months. LUCENTIS® is also approved in the United States for macular edema following retinal vein occlusion (RVO) using 0.5 mg (0.05 mL) on a once-a-month intravitreal regimen. In addition, LUCENTIS® is approved in Europe and in the United States for diabetic macular edema in the injectable formulation.

Sunitinib (SU-11248, Sutent), was approved January 2006 by FDA as a monotheraphy for the treatment of metastatic renal cell cancer and gastrointestinal stromal tumors. Sunitinib inhibits at least eight receptor protein-tyrosine kinases including vascular endothelial growth factor receptors 1-3 (VEGFR1-VEGFR3), platelet-derived growth factor receptors (PDGFRα and PDGFRβ). This compound inhibits angiogenesis by diminishing signaling through VEGFR1, VEGFR2, and PDGFRβ, PDGFRβ is found in pericytes that surround capillary endothelial cells [1](Roskoski, 2007, PDF document attached). There is evidence that the combined use of an anti-PDGF is superior to ranibizumab monotherapy in the treatment of some VEGF related diseases.

There are multiple side effects or potential side effects including patient discomfort associated with the intravitreal injection of anti-VEGF antibodies and other ophthalmic drugs. The intravitreal injection procedure requires a dedicated clean room with ordinary aseptic rules; resuscitation facilities must be immediately available. Complications of this procedure include infectious endophthalmitis; retinal detachment and traumatic cataract. Other possible complications of intravitreal injection include intraocular pressure changes, especially intraocular pressure elevations. Injection related intraocular pressure elevations which can occur immediately after injection of any kind of medication and drug specific-related intraocular pressure changes which may be detected days or even months after the injection. See Semin. Ophthamol. 2009 March-April; 24(2):100-5.

There is an urgent unmet medical need for new topical treatment regimens of such anti-VEGF antibodies and other effective ophthalmic drugs such as antimicrobials, antivirals, corticosteroids and anti-vascular endothelial growth factor agents which are the main classes of drugs that are administered through intravitreal injections. The present invention comprises a combination of said liposomes and any of said drugs within said drug classes in a topical formulation. While U.S. Pat. No. 6,884,879 generally discloses various possible delivery methods or reagents including liposomes and various routes of administration including topical administration of such VEGF monoclonal antibodies, the only approved form of ranibizumab is the intravitreal form in a liquid formulation. There is a need for topical ranibizumab formulations that are effective in treating people having VEGF related disorders including ophthalmic disorders.

The inventors have met this unmet need and have surprisingly found that certain liposomal formulations comprising such VEGF monoclonal antibodies and certain liposomes provide effective relief in patients having diabetic macular edema. The formulations can be effectively administered topically to the affected eye and are more effective than topical application of the intravitreal formulation. U.S. Pat. No. 6,958,160 discloses and claims self-forming, thermodynamically stable liposomes. United States Pat. Pub. No. 2010/0076209, hereby incorporated by reference, discloses PEG-lipid conjugates for liposomes and drug delivery. Various lipid based products including such self-forming thermodynamically stable liposomes marketed under the brand name Qsomes™ (hereinafter Qsome) are sold by Biozone Laboratories for multiple therapeutic uses and via various routes of administration including by topical administration to the skin. The inventors have discovered that a pharmaceutical composition comprising ranibizumab and such self forming, thermodynamically stable liposomes and/or PEG-lipid conjugates can be delivered topically to the eye of a patient in need of treatment of VEGF related ophthalmic diseases and conditions. The present invention further comprises a topical formulation comprising a Qsome as recited herein (self-forming thermodynamically stable liposome) and a drug wherein the formulation is suitable for the treatment of a posterior segment ophthalmic disease and/or a disease that is a combination anterior segment/posterior segment disease. The claimed formulations are suitable for topical administration and are particularly useful in treating ophthalmic diseases and conditions that are typically treated via a periocular route or via intravitreal administration (intraocular delivery). Periocular administration includes subconjunctival, subtenon, retrobulbar and peribulbar administration. There are some drugs that have been disclosed as being able to be delivered to the posterior segment by topical administration—these include ESBA 105, an anti-TNF-alpha single chain antibody; dexamethasone; nepafenac; memantine HCl; dorzolamide; brimonidine and betaxolol. It is believed that topical administration of these drugs in a Qsome formulation will result in more effective topical delivery and more effective posterior segment delivery. Preferably, however, the claimed invention comprises a topical formulation including a Qsome liposome as described herein and drugs which heretofore have not been effectively delivered through topical administration.

Drugs typically given by intravitreal injection include antimicrobials, antivirals, corticosteroids and anti-vascular endothelial growth factor agents. The present invention comprises a liposomal formulation comprising a self-forming thermodynamically stable liposome and an active pharmaceutical agent selected from any one of or a combination of an antimicrobial, antiviral, corticosteroid and anti-vascular endothelial growth factor agent wherein said formulation is suitable for topical delivery to the eye of a patient to treat an ophthalmic disease or condition. Diclofenac, gatifloxacin, sparfloxcain lactate, GCV, demeclocycline, flubiprofen, doxorubicin, celecoxib, budesonide and cisplatin have been formulated in colloidal dosage forms for transcorneal or transcleral delivery. Cationic liposomes containing penicillin G, tropicamide and acetazolamide have been used to provide maximum drug transport across the cornea relative to anionic and neutral liposomes. See Schaeffer et al. Liposomes in topical drug deliver. Invest. Ophthalmol. Vis Sci. 1982:22(2):220-7; Nagarsenker et al. Preparation and evaluation of liposomal formulations of tropicamide for ocular delivery. Int J Pharma. 1999:190(1):63-71 and Hathout et al. Liposome as an ocular delivery system for acetazolamide: in vitro and in vivo studies. AAPS PharmaSciTech. 2007; 8(1): 1.

Diabetic retinopathy (DR) is the most common microvascular complication of diabetes (Fong, 2004) and is the leading cause of new cases of vision loss among working-aged adults. Diabetic macular edema (DME) is the most common cause of vision loss in patients having DR. The prevalence of DME is 3% recent diagnosis with about 75,000 new cases of DME each year (USA). The number of worldwide patients having diabetes is a staggering 285 million. DME results from a series of biochemical and cellular changes that ultimately cause progressive leakage and exudation, leading to thickening of the retina and hard exudates within 1 disc diameter of the center of the macula. DME is one of the most common causes of impaired vision in patients with diabetes (Bhagat, 2009). Approximately 50% of patients experience a loss of ≥2 lines of BCVA after two years of follow-up (Meyer, 2007).

In DME, damaged blood vessels leak fluid into the central portion of the retina (macula) which leads to swelling. The macula is involved with sharp central vision. The fovea is at the center of the macula. DME can occur in patients having type 1 or type 2 diabetes. Approximately 26 million people in the United States have diabetes and 1.9 million new cases are diagnosed in people aged 20 and older each year. Up to 75,000 new cases of DME are estimated to develop each year. DME is a leading cause of blindness among the working-age population in most developed countries. First line therapy for DME is laser surgery which seals the leaky blood vessels to diminish the leakage of fluid and reduce the amount of fluid in the retina. There is thus a significant need to create new formulations that provide therapeutic relief to these patients. In addition to DME, cystoid macular edema and branch vein retinal occlusion and central vein retinal vein occlusion may be treated by the formulations of the invention.

SUMMARY OF THE INVENTION

The present invention is a pharmaceutical formulation comprising an ophthalmic drug and a thermodynamically stable liposome. The preferred drugs are selected from an anti-angiogenic compound or other ophthalmic active ingredient. The preferred anti-angiogenic compounds are anti-VEGF antibodies. The preferred drugs are also steroids. The pharmaceutical formulation is preferably administered as a topical formulation to the eye of a patient in need of treatment thereof. In some cases, the formulation may be suitable to deliver in an intravitreal injection but with less frequent injections than those administered with current treatments such as LUCENTIS®. The pharmaceutical formulation is useful in the treatment of a wide range of ophthalmic disorders including VEGF related ophthalmic disorders including, for example, age related macular degeneration and diabetic macular edema and other forms of macular edema or diabetic retinopathy. The present invention is also directed to formulations suitable for topical administration and which are effective in treating corneal neovascular disease.

The preferred anti-VEGF antibody is selected from ranibizumab (LUCENTIS®) and may be prepared as described in U.S. Pat. No. 6,884,879 which is hereby incorporated-by-reference. This product is sold as a prescription intravitreal liquid formulation. Ranibizumab is a recombinant humanized IgG1 kappa isotype monoclonal antibody fragment. This antibody binds to and inhibits VEGF-A and has a molecular weight of approximately 48 kilodaltons. The product is produced in an *E. coli* expression system in a nutrient medium that contains tetracycline. The prescription product is supplied in a single use glass vial containing 0.05 mL of a 10 mg/mL of ranibizumab. Other anti-VEGF antibodies such as bevacizumab may also be used to treat certain diseases and conditions such as corneal neovascular disease. The topical liposomal formulation disclosed herein facilitates penetration of whole antibodies such as bevacizumab into eyes having abnormal neovascularature. This compound may also be prepared by other suitable recombinant means.

The liposomes useful in the present invention preferably comprise those liposomes that are described in U.S. Pat. No. 6,958,160 which is hereby incorporated by reference in its entirety. As described therein, liposomes are self-closed colloidal particles wherein membranes composed of one or more lipid bilayers encapsulate a fraction of the aqueous solution in which they are suspended. As also recited in the '160 patent, not all liposomes are the same and, in fact, liposomes can have problems including colloidal instability and manufacturing issues due to extreme conditions such as elevated pressures and temperatures as well as high shear conditions-all of which can degrade the lipid components. Other issues associated with liposomes in general can include heterogeneous distributions of sizes and numbers of bilayers which can cause or acerbate scale-up issues. In addition, sterilization conditions can also create issues with liposomes. Liposomes also may have colloidal instability due to aggregation while in suspension. This leads to fusion issues and the solution to this problem is typically lyophilization which is a costly extra step. The liposomes disclosed in the '160 patent have overcome these problems and it has been surprisingly found that these particular liposomes are effective when combined with anti-VEGF antibodies such as ranibizumab.

In particular, a formulation comprising self-forming, thermodynamically stable liposomes and an anti-VEGF antibody is particular suitable for topical application in the treatment of VEGF related ophthalmic diseases and conditions.

The liposomes useful in the present formulation comprise diacylglycerol-PEG compounds. The melting point of these compounds is below about 40° C. and the acyl chains are greater than or equal to about 14 carbons in length. These compounds are prepared as recited in the '160 patent. The preferred lipid PEG conjugate is PEG-12-GDM (Polyethylene glycol 12-Glycerol Dimyristate). PEG stabilizes the liposomes by creating a steric barrier at the outer surface of the liposomes, the PEG chain has a molecular weight between about 300 Daltons and 5000 Daltons. Liposome preparation entails merely mixing the lipid with an aqueous solution. These kinds of liposomes exist in the lowest energy state that the lipid can exist in while in aqueous solution, reproducibility of liposome formation is no problem.

A defined lipid, lipid mixture, or lipid/compound mixture will form similar liposomes every time when mixed with the same aqueous solution. Above critical concentrations (around 20% weight to volume) non-liposomal structures will begin to form in aqueous solution. These liposomes exist in their lowest energy state and are thermodynamically stable, self-forming liposomes. PEG-12 GDM forms very small vesicles so they can be sterile filtered. Kinetic energy, such as shaking or vortexing, may be provided to the lipid solution and the aqueous solution. The present formulation may also use other lipid-PEG conjugates as generally or specifically described in the U.S. Pat. No. 6,958,160 patent. In addition, other lipid PEG self-forming, thermodynamically stable conjugates may also be used including those compounds described in US Pat. Pub. No. 2010/0076209. The Table below describes certain PEG-12 GDM characteristics.

TABLE

| PEG-12 GDM CHARACTERISTICS: | | | | | |
|---|---|---|---|---|---|
| LIPID | MELTING POINT (° C.) | Pa | Pv | SPONTANEOUS LIPOSOMES AT 20° C. | SPONTANEOUS LIPOSOMES AT 37° C. |
| PEG-12 GDM | Fluid @ 25 | 0.829 | 0.869 | YES | YES |

MOLECULAR WEIGHT: 1068 g/mol
OPTIMUM pH: 5-7
SOLUBILITY: Soluble in organic solvents.

In the ranibizumab topical formulation of the present invention, 1% weight volume of PEG-12 GDM based upon the final volume of solution was used and having a pH of the topical solution of 5.5 and in the appropriate range of working with the liposome.

In addition to the anti-angiogenic compound (e.g. the anti-VEGF antibody) and the thermodynamically stable, self-forming liposome, the formulation may further comprise additional pharmaceutically acceptable excipients. The preferred excipients are selected from the group consisting of excipients suitable for topical administration to the eye. These include surfactants, buffer reagents, pH modifiers, salts and other such ingredients.

The formulations are useful in treating VEGF related diseases and conditions and/or other angiogenic conditions. The present invention thus includes use of such formulations to treat age related macular degeneration, diabetic retinal diseases including diabetic macular edema and corneal neovascularization. In a preferred embodiment, the invention comprises a topical formulation and encompasses a method of treating such VEGF related diseases and conditions by topically administering such formulations to the eye of a patient in need of treatment thereof.

BRIEF DESCRIPTION OF THE DRAWINGS

The invention will be described in the following figures.

FIG. 1 shows improvement in CFT occurring again from the 12 week to 14 week period.

FIG. 1 shows improvement in VA occurring again from the 12 week to 14 week period.

DETAILED DESCRIPTION

Figure 1:
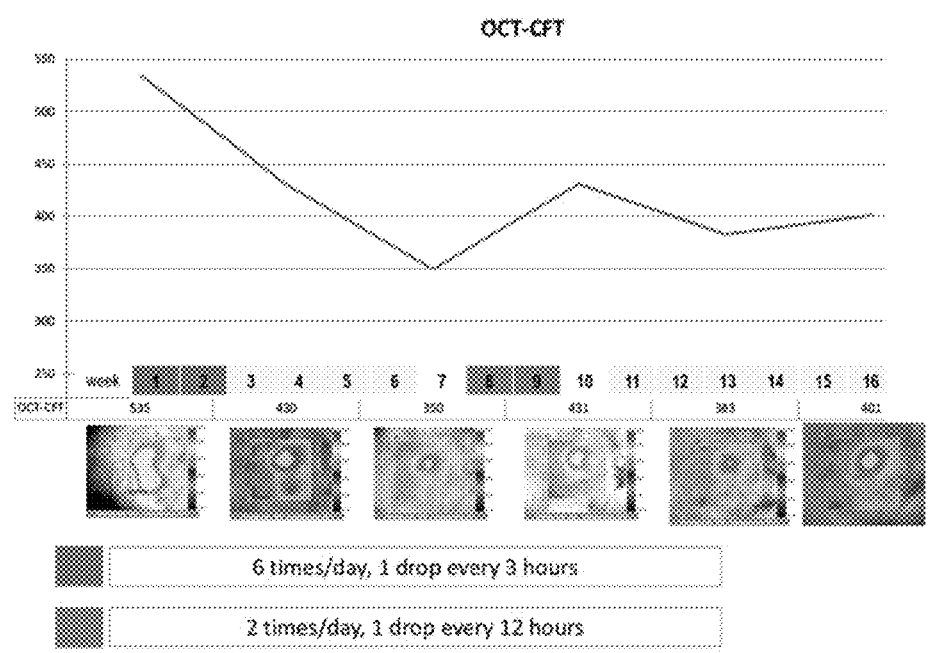
FIG. 1 shows data from a single patient treated with a liposomal ranibizumab formulation having improved central foveal thickness measurements using optical coherence topography (OCT-CFT) over an eight week period after being dosed six drops per day for two weeks. At week eight the patient showed an increase in CFT and treatment was reinitiated at 10 weeks at a daily dose of 2 drops per day.

The present invention relates to pharmaceutical formulations and uses thereof wherein the preferred formulation comprises an anti-VEGF antibody and a self-forming, thermodynamically stable liposome. The present invention also relates to a topical formulation comprising an anti-VEGF antibody and a self-forming, thermodynamically stable liposome. The invention further comprises a method of treating a VEGF related disease or condition comprising administration of a formulation comprising an anti-VEGF antibody and a self-forming, thermodynamically stable liposome to a patient in need of treatment thereof. In a preferred embodiment the VEGF related disease or condition is selected from a diabetic retinopathy (DR).

While liposomes "in general" have been described in connection with the delivery of various active ingredients, the art does not disclose or teach the combination of self-forming, thermodynamically stable liposomes in combination with anti-VEGF antibodies. The liposomes of the formulation are particularly suitable for delivery of anti-VEGF antibodies to a patient in need of treatment of a VEGF-related disease or condition and, in particular, to ophthalmic diseases or conditions. The liposomal formulations of the present invention are particularly suited for topical administration to the eye of a patient in need of treatment of, for example, diabetic macular edema or age-related macular degeneration or corneal neovascularization. The liposomes of the present invention have desired fundamental properties that make them especially suitable for these topical formulations. The liposome suspensions are thermodynamically stable at the temperature of formulation. The compositions of the lipids that make up the liposome have several fundamental properties. The lipids have packing parameters that allow the formation of liposomes. The lipids include, as part of the head group, a polyethyleneglycol (PEG) or polymer of similar properties that sterically stabilizes the liposomes in suspension. In addition, the liposomes have a melting temperature that allows them to be in liquid form when mixed with water or an aqueous solution.

As described in the U.S. Pat. No. 6,610,322 patent, little or no energy need be added when forming the liposomal suspensions in aqueous solution. In the present invention, the preferred method involves forming the liposomal suspension in the presence of an aqueous solution containing the active ingredient-the anti-VEGF antibody. Self-assembly thus preferably occurs with the active ingredient rather than before the active ingredient is added to the suspension. The lipid molecules disperse and self assemble into the natural low energy state. The liposomes form large or small unilamellar vesicles (SUVs) or multilamellar vesicles (MLVs) (see FIG. 3) and as described in the Biozone Laboratories website for Qusomes™.

The PEG chain preferably has a molecular weight of between about 300 Daltons and 5000 Daltons. Examples of suitable lipids include PEG-12 GDO (glycerol dioleate) and PEG-12 GDM (glycerol dimyristate). PEG-12 GDM is fluid at 25° C. and has packing parameters $P_a$ and $P_v$ of 0.853 and 0.889 respectively. Each of these lipids form spontaneous liposomes at 20° C., 37° C. and 60° C. The Pa may range between 0.84 and 0.88 and the $P_v$ between about 0.88 and 0.93. Preferably, the suitable compounds form liposomes instead of, for example, micelles. In addition, the lipid composition should have a phase transition temperature of between about 0° C. and 100° C.-the lipid composition has a melting temperature which allows the composition to be in liquid form when mixed with an aqueous solution. Also, the bending elastic modulus of the composition should be such that the lipid composition can form liposomes in an aqueous environment without the need for any or any significant energy input. Kinetic energy may be applied to the solution. The preferred bending elastic modulus is between about 0 kt and 15 kt. The bending elastic modulus is largely determined by the backbone and glycerol is a preferred backbone of the present invention although any equivalent backbone in terms of bending elastic modulus and suitable functionality may also be used. The relative percentage by weight of the lipid in the final solution may range from greater than 0 to about 20 wt percent (w/w). The range may be between about 1% and 15 wt % or between about 1% and 10% or between about 1% and 5% wt/wt or between greater than 0% and 4% wt/wt.

Mixtures of other molecules and lipids having PEG chains longer than 12 may also be used in the present invention provided they form liposomes. For example mixtures of PEG-45 GDS (glycerol distearate) and cholesterol forms liposomes. As described in the '322 patent, one of ordinary skill in the art can vary the variables including PEG chain length and components to prepare a thermodynamically stable, free forming liposome and such are included within the scope of the present invention and when combined with an anti-VEGF antibody. The amount of cholesterol when added to the lipid before liposomal formation is up to about 10% w/w.

In addition to the lipids described in the '322 patent, other lipids may also be utilized in the present invention. U.S. Pat. Pub. No. 2010/0076209 describes certain PEG-LIPID conjugates that form liposomes suitable for drug delivery of specifically described active ingredients. There is no teaching of or reference to the delivery of anti-VEGF antibodies in the reference. In particular, diacylglycerol-polyethylene glycol compound as described in the '209 publication may be utilized in combination with anti-VEGF antibodies in the formulations of the present invention. The general structure of the lipid compounds is shown in the '209 publication and includes compounds having the formula (R2)(R1)Glycerol-X-PEG-R1 and/or R1-PEG-X-Glycerol(R2)(R1) wherein R1 is preferably either —OH or —OCH3; R2 and R3 are fatty acids including and not limited to laurate, oleate, myristate, palmitate, stearate and linoleate; and X represents a single linker or replicate linkers or combination of two or more linkers in between the lipid and PEG. R2 and R3 may be the same or different. If R2 is at the C1 position of glycerol, R3 can be located at either C2 or C3. The general structure includes all racemers and structural isomers and/or functional equivalents thereof.

R1 may also be selected from, for example, —NH2, —COOH, —OCH2CH3, —OCH2CH2CH3,

—OCH2CH2OH, —COCH═CH2, —OCH2CH2NH2, —OSO2CH3, —OCH2C6H6, —OCH2COCH2CH2COO-NC4H4O2, —CH2CH2═CH2 and —OC6H6. Also R1 may be a functional group that helps link or links therapeutic or targeting agents to the surface of a liposome. These may include amino alkyl esters, maleimide, diglycidyl ether, maleinimido propioinate, methyl carbamate, tosyhydrazone salts, azide, propargyl-amine, propargyl alcohol, NHS esters, hydrazide, succinimidyl ester, succinimidyl tartrate, succinimidyl succinate, and toluesulfonate salts. The present invention includes liposomal formulations having anti-VEGF antibodies within the liposomal composition and may further include any other therapeutic compound including the anti-VEGF antibodies covalently bound or linked to the liposome via the R1 functional group. In such instance, the invention would include or be a combination formulation or a formulation having both a non-covalently bound active ingredient and a covalently bound active ingredient wherein said active may be the same or different.

The linkers useful or suitable in this type of liposomal formulation include those described in the '209 publication and which is hereby incorporated by reference. Table 1 therein describes or lists such suitable linkers and which include amino, succinylamino acetamido, 2-aminopentanamido, 2(2')-R'-aminoacetyl etc. In each case, the lipids form spontaneous liposomes at 20 and 37° C. as shown in Table 4 of the '209 publication. The present invention thus includes those lipids described as PEG-12-N1-GDO; PEG-23-N2-GDO; PEG-18-N3-GDO; PEG-23-N4-GDO; PEG-8-S1-GDO; PEG-18-S2-GDO; PEG-12-S3-GDO; PEG-18-Ac1-GDO; PEG-12-Ac2-GDO; PEG-12-N1-GDM; PEG-12-N1-GDLO; PEG-12-S3-GDM; PeG-12-S3-GDLO; PEG-12-Ac2-GDM; PEG-12-Ac2-GDLO; PEG-23-N1-GDL; PEG-2kNI-GDP; PEG-23-Ac2-GDL and PEG-12-Ac2-GDP. GDLO means glycerol dilinoleate and GDP means glycerol dipalmitate. Each of the compounds are fluid at 25° C. and have packing parameters Pa ranging from 0.830 to 0.869 and Pv ranging from 0.872 to 0.924.

The present invention further includes known lipids that meet the physical requirements recited herein and which, for example, are liquid at 25° C. and are self-forming at both 20° C. and 37° C. and have functionally equivalent or equivalent packing parameters and form thermodynamically stable liposomes with little or no energy input when combined with an aqueous solution.

The anti-VEGF antibodies useful in the present formulation include any known anti-VEGF antibody. These antibodies include whole antibodies or antibody fragments provided they have the requisite anti-VEGF biological properties. In a preferred embodiment, the antibody is an antibody fragment having the requisite anti-VEGF biological and pharmacological properties. U.S. Pat. No. 6,884,879 discloses anti-VEGF antibodies useful in the present invention. Such antibodies include humanized anti-VEGF antibodies and anti-VEGF antibody variants with properties that include strong binding affinity for VEGF; the ability to inhibit VEGF promoted proliferation of endothelial cells and the ability to inhibit VEGF induced angiogenesis. The preferred binding affinity (Kd) is no more than about $5 \times 10^9 M$ and with an ED50 value of no more than about 5 nM for inhibiting VEGF-induced proliferation of endothelial cells in vitro. The antibodies include those that inhibit at least about 50% tumor growth in an A673 in vivo tumor model at an antibody dose of 5 mgs/kg. The most preferred antibody is sold under the brand name LUCENTIS® (ranibizumab) and is approved for the treatment of age-related macular degeneration and various forms of macular edema as an intravitreal formulation. The term "anti-VEGF antibody" includes whole antibodies as well as antibody fragments. The range of diseases that can be treated with anti-VEGF antibodies includes those diseases or conditions that are associated with angiogenesis or pathological angiogenesis conditions. These include cancer as well as intraocular neovascular syndromes such as proliferative retinopathies or age-related macular degeneration (AMD), rheumatoid arthritis and psoriasis. While the preferred route of administration is topical treatment to the eye and the preferred disease modality is diabetic macular edema, the formulation recited herein may also be useful in other delivery modes (i.e., injectable; intravenous infusion) and in the treatment of the litany of VEGF related diseases and conditions.

The anti-VEGF antibodies include those produced from an isolated nucleic acid encoding a humanized variant of a parent anti-VEGF antibody which parent antibody comprises non-human variable domains, wherein said humanized variant binds human VEGF and has those heavy chain Complementary Determining Region amino acid sequences as described and claimed in the U.S. Pat. No. 6,884,879 patent which is hereby incorporated by reference. The anti-VEGF antibodies include those that can be produced using vectors having nucleic acid encoding such CDR amino acid sequences and isolated host cells containing such vectors. The host cells can be cultured to produce such sequences and the humanized anti-VEGF antibodies may be recovered from such host cell cultures. The isolated nucleic acid recited above may further encode for a humanized variant having a light chain Complementary Determining Region (CDR) with those sequences as recited in the '879 patent. Such humanized variant may comprise a heavy chain variable domain and a light chain variable domain having sequence as described in the '879 patent. Such humanized variant may also comprise a heavy chain variable domain sequence and a light chain variable domain sequence as shown in the '879 patent.

U.S. Pat. No. 7,060,269 is also incorporated by reference herein. This patent claims and discloses ranibizumab. Claim 1 of the '269 patent claims a method for inhibiting VEGF-induces angiogenesis in a subject, comprising administering to said subject an effective amount of a humanized anti-VEGF antibody which binds human VEGF with a Kd value of no more than about 1×10, said humanized anti-VEGF antibody comprising a heavy chain variable domain sequence and a light chain variable domain sequence. Ranibizumab is a recombinant humanized IgG1 kappa isotype monoclonal antibody fragment designed for intraocular use. This monoclonal antibody binds to and inhibits human vascular endothelial growth factor A (VEGF-A). Ranibizumab has a molecular weight of about 48,000 daltons and is produced in an *E. coli* expression system in a nutrient medium containing tetracycline. This product is commercially available under the tradename LUCENTIS® and is supplied as a preservative free, sterile solution in a single use glass vial that can deliver 0.05 mL of 10 mg/mL ranibizumab aqueous solution with 10 mM histidine HCl, 10% alpha, alpha trehalose dehydrate, 0.01% polysorbate 20, and at a pH of 5.5.

Ranibizumab is described in a scientific journal published in 1999 in the Journal of Molecular Biology (JMB) by Chen et al. entitled "Selection and Analysis of an Optimized Anti-VEGF Antibody: Crystal Structure of an Affinity-matured Fab in complex with Antigen" [5](Chen et al. JMB, 293:865-881 (1999). The heavy chain and light chain sequences of ranibizumab are designated as YO317 in this article and are shown in Figure 1 therein. In addition to this description, the article also provides data regarding binding affinity of this antibody fragment to VEGF (Table 6 on page 870 therein). Ranibizumab is known to bind to and inhibit the biological activity of VEGF-A which causes neovascularization and leakage in ocular angiogenesis models. Ranibizumab binds to and inhibits VEGF-A and prevents VEGF-A from interacting with the VEGF receptors on the surface of endothelial cells and thus reduces new blood vessel formation (angiogenesis); vascular leakage and endothelial cell proliferation. Administration of a pharmaceutically effective amount of ranibizumab inhibits VEGF induced angiogenesis. The term anti-VEGF antibody encompasses full length antibodies and antibody fragments such as Fab, Fab', $F(ab)_2$ and $F_v$ provided said fragments show the desired pharmacological activity by binding to human VEGF. Ranibizumab has a binding affinity to VEGF (Kd) of no more than about $1 \times 10^{-8}$ M—i.e., of about $1.4 \times 10^{-10}$ (see Chen et al. on page 870). FIGS. 10A and 10B of the '269 patent provide the sequences of the light chain variable and heavy chain variable domains of ranibizumab (Fab Y0317 as shown in Chen et al.). These sequences are identical to those shown in the '269 patent.

In addition to ranibizumab and other anti-VEGF inhibitors or drugs described in the above articles and patents, additional anti-VEGF or anti-angiogenic drugs may also be utilized in the present formulation. While the inventors have discovered that anti-VEGF antibodies that are antibody fragments are preferred in the liposomal formulations for the treatment of diseases and conditions that involve topical application to the eyes of patients having healthy corneas or di minimus neovascularization of the cornea but some other ocular condition (e.g. age related macular degeneration or diabetic macular edema), formulations comprising whole anti-VEGF antibodies and self-forming, thermodynamically stable liposomes are also useful in the treatment of corneal neovascularization and these other ocular diseases (in patients having both diseases) provided the corneal neovascularization permits or facilitates the entry of the large whole antibody and formulations thereof. An example of an intact or whole anti-VEGF antibody is sold by Genentech under the brand name AVASTIN® (bevacizumab). This antibody is a recombinant humanized IgG1 antibody that inhibits the biological activity of VEGF. It contains human framework regions and the complementarity-determining regions of a murine antibody that binds to VEGF and has an approximate molecular weight of 149 kD. This antibody is produced in a mammalian cell (Chinese Hamster Ovary) expression system in a nutrient medium containing Gentamycin. U.S. Pat. No. 6,054,297 (hereby incorporated by reference in its entirety) claims and discloses bevacizumab or a process for making bevacizumab (see claims 1, 6, 7, 8, 9, 10, 12, 29 and 30 therein).

As described in the approved product package insert, bevacizumab is a recombinant humanized monoclonal IgG1 antibody that binds to and inhibits the biological activity of human vascular endothelial growth factor in in vitro and in vivo assay systems. This antibody contains human framework regions of a murine antibody that binds to VEGF (see L. G. Presta et al. (1997) Cancer Res. 57: 4593-99). The molecular weight of bevacizumab is about 149 kilodaltons. This paper discloses the interaction of the variable domains of the humanized F(ab) antibody fragment, "F(ab)1-12." Bevacizumab has non-human CDRs derived from the sequence of murine antibody as well as framework substitutions in the variable domains at position 46 in the light chain ($V_L$) and positions 49, 69, 71, 73, 78 and 94 in the heavy chain ($V_B$) that are the same as the substitutions shown at the corresponding positions of F(ab)-12, as shown in FIG. 1 of Presta et al. Presta et al. has information about the molecular features and binding characteristics of bevacizumab.

Figure 7:
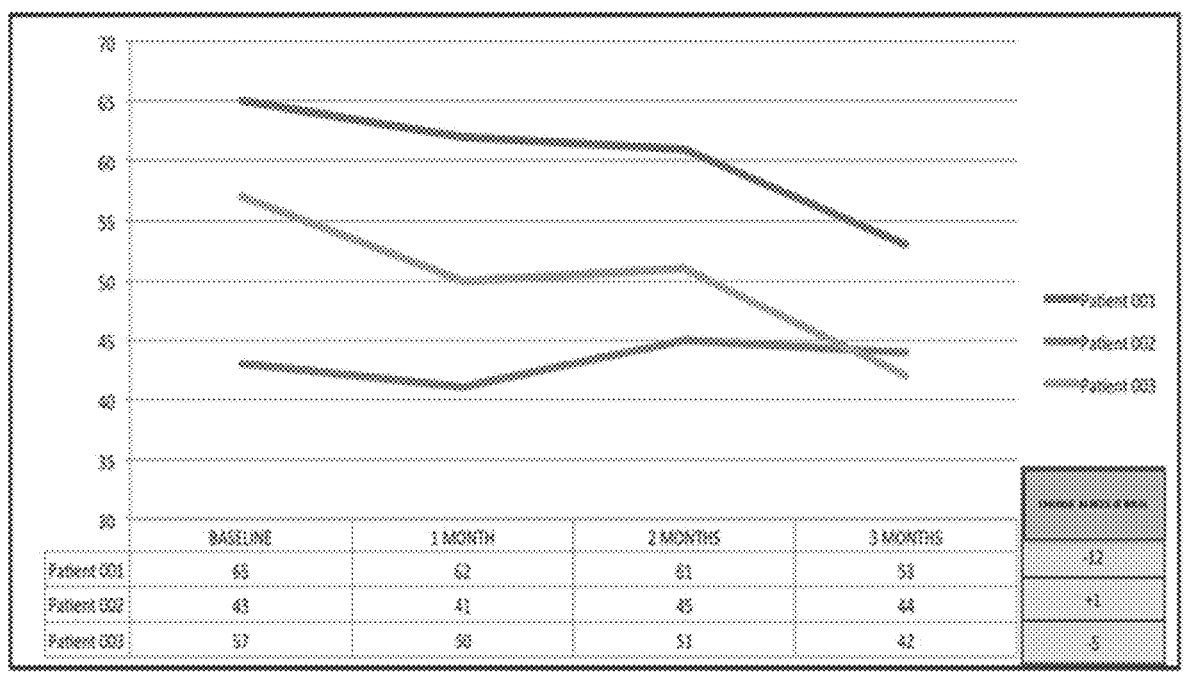
FIG. 7 shows the results of BCVA over time for the contra-lateral eyes.

As stated previously, In addition to ranibizumab and bevacizumab, other known anti-VEGF antibodies or anti-angiogenic drugs may also be utilized in the present invention. The anti-VEGF antibodies of the invention are prepared as described in the patent references cited above with respect to same. In general, isolated nucleic acid encoding the antibody; vectors comprising the nucleic acid are operably linked to control sequences recognized by host cells transformed with the vector; host cells having said vector are all collectively used in a process for producing the antibody of interest after culturing said cells and collecting and purifying the antibody. Any suitable pharmaceutical excipient may be added to the antibody and the antibody may also be lyophilized as desired. The "anti-VEGF antibodies" are inclusive of various forms and may be full length having an intact human Fc region or an antibody fragment—e.g. Fab, Fab' or $F(ab')_2$. The other anti-angiogenic drugs suitable for combining with the lipids disclosed herein to form liposomal formulations include pegaptanib or etanercept (a TNF inhibitor). In the latter case, this formulation may be used to treat various autoimmune diseases or conditions. Etanercept is sold under the trade name Enbrel® which is used to treat rheumatoid, juvenile rheumatoid and psoriatic arthritis, plaque psoriasis and ankylosing spondylitis. Other suitable drugs include sunitinib, a VEGF and PDGF receptor protein kinase and angiogenesis inhibitor (a 2-oxindole sold under the name SUTENT®) and which is described and claimed in U.S. Pat. No. 6,573,293 hereby incorporated by reference) or FOVISTA™ (formerly known as E10030), a regulator of platelet derived growth factor B (PDGF-B) (1.5 mgs/0.5 mgs ranibizumab). Other suitable drugs used in combination include interferon-alpha-2a or temsirolimus or other mTOR inhibitors such as rapamycin. Classes of drugs for ocular diseases that may be used in combination also include proteasomal inhibitors, autophagy inhibitors, retinoids, lysosomal inhibitors, heat shock response activators, Hsp90 chaperone inhibitors, protein transport inhibitors, glycosidase inhibitors, tyrosine kinase inhibitors and histone deacetylase inhibitors. These drugs may be utilized alone in the liposomal formulation or may be used in a combination formulation with an anti-VEGF compound or antibody or may be used in sequential combination and preferably in a topical formulation. The preferred indication when combining FOVISTA™ (0.03-3.0 mgs/eye in combination with 0.5 mg ranibizumab or other anti-VEGF compound) (and/or other drug having PDGF inhibition activity) and ranibizumab is the treatment of age-related macular degeneration. Aflibercept (2.0 mgs/0.05 mL) (Eylea™) may also be used in the liposomal formulation alone or in combination with ranibizumab or other active ingredients. The present invention further includes a topical liposomal formulation as recited herein comprising FOVISTA and aflibercept and/or any other anti-angiogenic drug provided that at least one of the active ingredients is blended/combined with the thermodynamically stable, self forming liposomes of the invention. FOVISTA (an aptamer directed against PDGF-B) is also known and described as "Antagonist A" in U.S. Pat. Pub. No. 2012/0100136 which is hereby incorporated by reference in its entirety. The synthesis of Antagonist A is described in Example 4 in the '136 publication (see also FIG. 7 therein). Each of the individual VEGF antagonists and PDGF antagonists described therein are also included in the scope of the present invention when at least one agent is formulated with a lipid described herein that forms a thermodynamically stable, self forming liposome. A topical formulation having any one of or any combination of the active ingredients recited herein is advantageous over the drugs or combination thereof, that are administered by intravitreal injection. In addition, topical application to the eye for an ocular disease is preferable to systemic oral administration. The compositions useful in the present invention include, as liposomal formulations or liposomal formulations and/or any other formulation in combination, (a) (PDGF inhibitors) ARC-127, Antagonist A, Antagonist B, Antagonist C, Antagonist D, 1B3 antibody, CDP860, IMC-3G3, imatinib, 162.62 antibody, 163.31 antibody, 169.14 antibody, 169.31 antibody, aRI antibody, 2A1E2 antibody, M4TS. 11 antibody, M4TS.22 antibody, A10, brefeldin A, sunitinib, Hyb 120.1.2.1.2 antibody, Hyb 121.6.1.1.1 antibody, Hyb 127.5.7.3.1 antibody, Hyb 127.8.2.2.2 antibody, Hyb 1.6.1 antibody, Hyb 1.11.1 antibody, Hyb 1.17.1 antibody, Hyb 1.18.1 antibody, Hyb 1.19.1 antibody, Hyb 1.23.1 antibody, Hyb 1.24 antibody, Hyb 1.25 antibody, Hyb 1.29 antibody, Hyb 1.33 antibody, Hyb 1.38 antibody, Hyb 1.39 antibody, Hyb 1.40 antibody, Hyb 1.45 antibody, Hyb 1.46 antibody, Hyb 1.48 antibody, Hyb 1.49 antibody, Hyb 1.51 antibody, Hyb 6.4.1 antibody, F3 antibody, Humanized F3 antibody, C1 antibody, Humanized C1 antibody, 6.4 antibody, anti-mPGDF-C goat IgG antibody, C3.1 antibody, 5-methyl-7-diethylamino-s-triazolo (1,5-a) pyrimidine, interferon, protamine, PDGFR-B1 monoclonal antibody, PDGFR-B2 monoclonal antibody, 6D11 monoclonal antibody, S is 1 monoclonal antibody, PR7212 monoclonal antibody, PR292 monoclonal antibody, HYB9610 monoclonoal antibody, HYB 9611 monoclonal antibody, HYB 9612 monoclonal antibody, HYB 9613 monoclonal antibody, 4-(2-(N-(2-carboxamido-indole)aminoethyl)-benzenesulfonate, 4-(2-(N-(-2-carboxamideindole)aminoethyl)-sulfonylurea, CGP 53716, human antibody g162, pyrazolo[3,4-g]quinoxaline, 6-[2-(methylcarbamoyl)phenylsulphanyl]-3-E-[2-(pyridine-2-yl)ethenyl]-indazole, 1-(2-[5-(2-methoxy-ethoxy)-benzoimidazole-1-yl]-quinoline-8-yl-piperidine-4-ylamine, 4-(4-[N-(4-nitrophenyl)carbamoyl]-1-piperazinyl]-6,7-dimethoxyquinazoline, 4-amino-5-fluoro-3-(6-(4-methyl-piperazine-1-yl)-1H-benzimidazole-2-yl)1H-quinoline-2-one, (4-tert-butylphenyl) {4-[(6,7-dimethoxy-4-quinolyl)oxy]phenyl}methaneone, 5-methyl-N-[4-(trifluoromethyl)phenyl]-4-izoxazolecarboxamide, trans-4-[(6,7-dimethoxyquinoxaline-2-yl)amino] cyclohexanol, (Z)-3-[(2,4-dimethyl-5-(2-oxo-1,2-dihydroindole-3-ylidenemethyl)-1H-pyrrole-3-yl)-propionic acid, 5-(5-fluoro-2-oxo-1,2-dihydroindole-3-ylidenemethyl)-2,4-dimethyl-1H-pyrrole-3-carboxylic acid, 1-(4-chloroanilino)-4-(4-pyridylmethyl)phthalazine, N-{4-(3-amino-1H-indazole-4-yl)phenyl-N"-(2-fluoro-5-methylphenyl)urea, 1,2-dimethyl-7-(2-thiophene)imidazole[5,4-g]quinoxaline, 1,2-dimethyl-6-phenyl-imidazolo[5,4-g]quinoxaline, 1,2-dimethyl-6-(2-thiophene)imidazolo[5,4-g]quinoxaline, AG1295, AG1296, 3-arylquinoline, 4-pyridyl-2-arylpyrimidine, sorafenib, MLN518, PKC412, AMN107, suramin, neomycin or a pharmaceutically acceptable salt thereof and (b) (VEGF inhibitors) ranibizumab, bevacizumab, aflibercept, KH902 VEGF receptor-Fe fusion protein, 2C3 antibody, ORA102, pegaptanib, bevasiranib, blunt ended bevasiranib, SIRNA-027, decursin, decursinol, picropodophyllin, guggulsterone, PLG101, eicosanoid LXA4, PTK787, pazopanib, axitinib, CDDO-Me, CDDO-mmnun, shikonin, betahydroxyisovalerylshikonin, ganglioside GM3, DC101 antibody, Mab 25 antibody, Mab73 antibody, 4A5 antibody, 4E10 antibody, SF12 antibody, VA01 antibody, BL2 antibody, BECG-related protein, sFLT01, sFLT02, Peptide B3, TG100801, sorafenib, G6-31 antibody or other compounds which inhibit VEGF related angiogenesis. In addition to antibodies, other protein based active ingredients suitable to treat ophthalmic diseases or conditions, including diseases of the front of the eye such as corneal diseases or healing necessary due to surgical incisions; trauma or ulcers, includes, for example, human growth hormones or other known hormonal peptides or variants thereof.

The liposomal formulation is prepared by following the following general steps in any order: (1) provision of an aqueous solution containing an anti-VEGF antibody and/or other active or actives as described above; (2) addition of a thermodynamically stable, self-forming lipid capable of forming a liposome to said aqueous solution of step (1) and (3) optional addition of pharmaceutically acceptable excipients. Any variation of a process to prepare the liposomal suspension formulation may be utilized including combining the anti-VEGF antibody (or VEGF inhibitor or PDGF inhibitor) and the lipid and then adding an aqueous solution or adding each ingredient separately to an aqueous solution. The suspension is prepared based upon the expected route of delivery (e.g. topical etc.) and the additional excipients are selected based upon such route as well. Carriers, stabilizers and/or excipients include buffers such as phosphate, citrate or other inorganic acids; antioxidants such as ascorbic acid and/or methionine; preservatives; low molecular weight polypeptides; proteins such as gelatin, serum albumin or immunoglobulins; hydrophilic polymers such as PVP; amino acids; monosaccharides or disaccharides or other carbohydrates; chelating agents; sugars; salt forming counter-ions; non-ionic surfactants and the like. The liposomal formulation may also be in the form of a solution.

The formulations are useful in the treatment of ophthalmic or VEGF related diseases and disorders. The preferred diseases or conditions to be treated with the formulation described herein are ocular diseases. As described above, the preferred disease or condition for the present invention is the treatment of diabetic macular edema and other forms of macular edema, cystoid macular edema, diabetic retinopathy, central retinal vein occlusion, branch retinal vein occlusion and are also useful as adjunct therapy in cataract surgery. As referenced above, DME results from a series of biochemical and cellular events that ultimately cause progressive leakage and exudation, leading to thickening of the retina and the formation of hard exudates within one disc diameter of the center of the macula. Laser photocoagulation is the mainstay of treatment and is effective to prevent the risk of moderate visual loss by about 505 [ETDRSRG, 1985]. Laser photocoagulation leads to improvement in reading line scores but has associated complication such as progressive enlargement of scars, central scotomata, decreased contrast sensitivity and impaired color vision.

The liposomal formulation may broadly treat tumors or retinal disorders associated with VEGF and/or PDGF or any other ophthalmic disease or condition depending upon the particular active ingredient. The anti-VEGF antibodies inhibit one or more of the biological activities caused by VEGF. Therapeutic applications involve a pharmaceutically acceptable dosage form administered to a patient in need of treatment of the particular disease or condition. Suitable dosage forms while preferably topical may also include administration by intravenous means as a bolus or by continuous infusion; intramuscular, intreperitoneal, intracerobrospinal, subcutaneous, intraarticular, intrasynovial, intrethecal, oral or by inhalation. In addition, such antibody formulations may also be administered by intra tumoral, peritumoral, intrelesional or perilesional routes. The neoplastic diseases amenable to treatment with the antibody formulations include various carcinomas including breast carcinoma, lung carcinoma, gastric carcinoma, esophageal, colorectal, liver, ovarian, arrhenoblastomas, cervical, endometrial, endometrial hyperplasia, endometriosis, fibrosacromas, choriocarcinoma, head and neck cancer, nasopharyngeal carcinoma, laryngeal carbinomas, hepatolastoma, Kaposi's sarcoma, melanoma, skin carcinomas, hemangioma, cavernous hemangioma, hemangioblastoma, pancreas carcinomas and other types of cancer. Non-neoplastic conditions that are VEGF related include rheumatoid arthritis, posriasis, atherosclerosis, diabetic and other proliferative retinopathies including retinopathy of prematurity, retrolental fibroplasias, neovascular glaucoma, age-related macular degeneration, diabetic macular edema and other forms of macular edema, thyroid hyperplasias including Grave's disease, corneal and other tissue transplantation, chronic inflammation, lung inflammation, nephritic syndrome, preeclampsia, ascites, pericardia effusions and pleural effusion. The preferred condition or disease treated with the preferred topical formulation is diabetic macular edema. The dosage administered and the frequency of administration will depend upon the type and severity of the disease and the particular patient's condition. For example, the anti-VEGF antibodies may be administered at a dosage range of 1 µg/kg to about 50 mg/kg or about 0.1-20 mg/kg to a patient in need of treatment thereof. The preferred dosage regimen for the treatment of DME and with respect to the topical formulation of ranibizumab is described in Example 3 herein. The concentration and amount of active ingredient may be varied depending upon the particular patient and the number of days treated and amount provided per day or week or month may also be varied depending upon the patient's response and signs of improvement in both visual acuity and in retinal thickening.

An ideal treatment modality for purposes of treating DME or other VEGF related ocular condition would be one that leads to rapid and long lasting vision improvement. The other treatment modalities currently used for the treatment of DME include selective PKCβ inhibitors (ruboxistaurin); steroids (triamcinolone acetonide, fluocinolone acetonide); VEGF inhibitors (bevacizumab; ranibizumab and pegaptinib-injectables) and vitrectomy. The present liposomal formulation provides a topical treatment regimen that is a significant improvement over, for example, intravitreal formulations currently on the market. The present formulation can be used in combination with other known treatments for the ocular or VEGF related diseases or conditions recited herein and/or as described above and provided there are no contraindications. Such treatment regimens or therapeutic approaches include, for example, siRNA molecules such as bevasiranib and with appropriate delivery vehicles including the thermodynamically stable, self forming liposomes utilized in the current invention.

Ophthalmic steroids that may be utilized in the liposomal formulation alone or in combination with any other active ingredient include dexamethasone, fluocinolone, loteprednol, difluprednate, fluorometholone, prednisolone, medrysone, triamcinolone acetonide, rimexolone and the various salt forms thereof. Other ophthalmic anti-inflammatory agents (for example NSAIDs) may also be utilized in the liposomal formulation. Depending upon the active ingredient, other liposomes in addition to or as an alternative to the thermodynamically stable self-forming liposomes may be utilized.

The following examples are intended to further illustrate certain embodiments of the invention and are non-limiting:

EXAMPLES

Example 1—A Solution of Liposomes and Ranibizumab

A vial containing 0.5 mg of ranibizumab at a concentration of 10 mg/mL (0.05 mL) was obtained. 0.015 grams of PEG-12 glycerol dimyristate (PEG-12 GDM) Qsomes™ was added to this solution (the number after PEG indicates the number of $C_2H_4O$ subunits in the PEG chain). The volume of this liposomal suspension was diluted to a final volume of 1.5 mL using 1.45 mL of a buffer solution consisting of phosphates, sodium chloride and polioxyl 40 stearate to provide a ranibizumab concentration of 0.333 mg/mL in the liposomal suspension and a lipid percentage of about 1% (10 mg/mL). Sodium perborate (0.28 mg/mL) was added as a preservative. 1 mL of this suspension is equivalent to 20 drops. Each drop contains approximately 17 µg ranibizumab.

Figure 3:
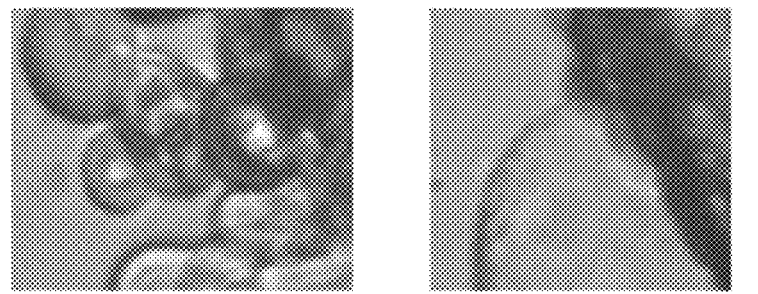
FIG. 3 shows microscopy pictures of multilamellar liposomes and unilamellar liposomes.
Figure 4:
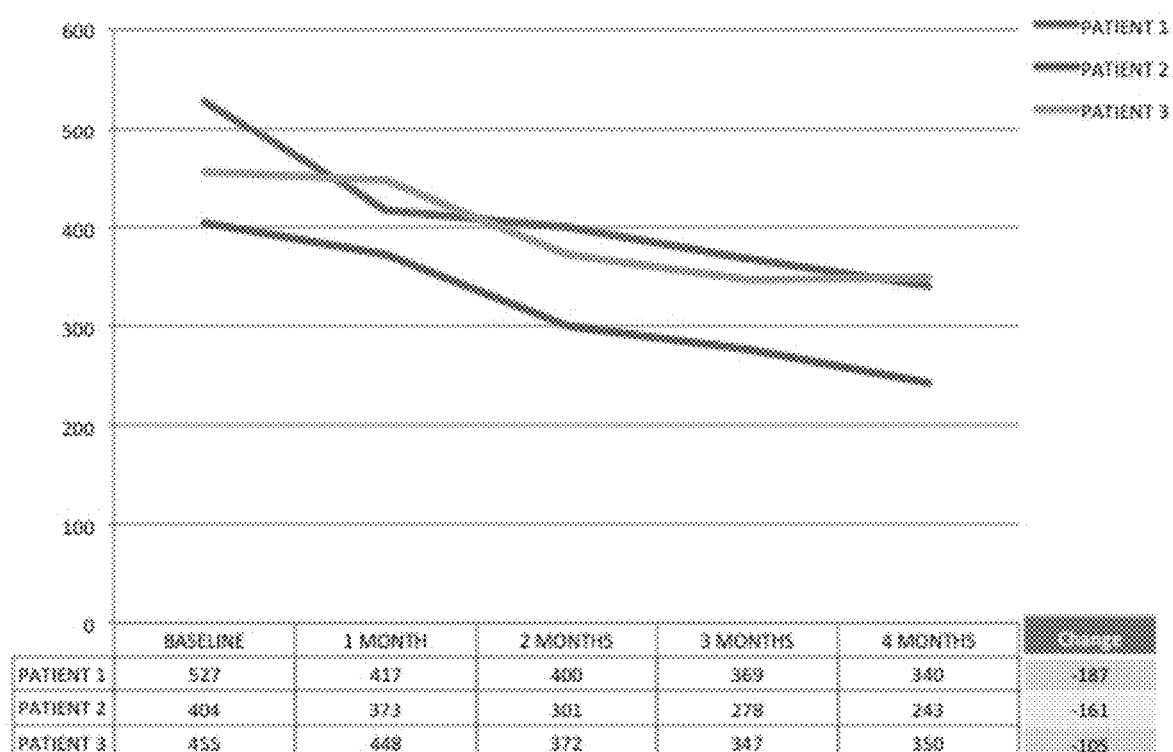
FIG. 4 shows OCT results of Central Foveal thickness of patients treated with the liposomal formulation of ranibizumab over time.
Figure 5:
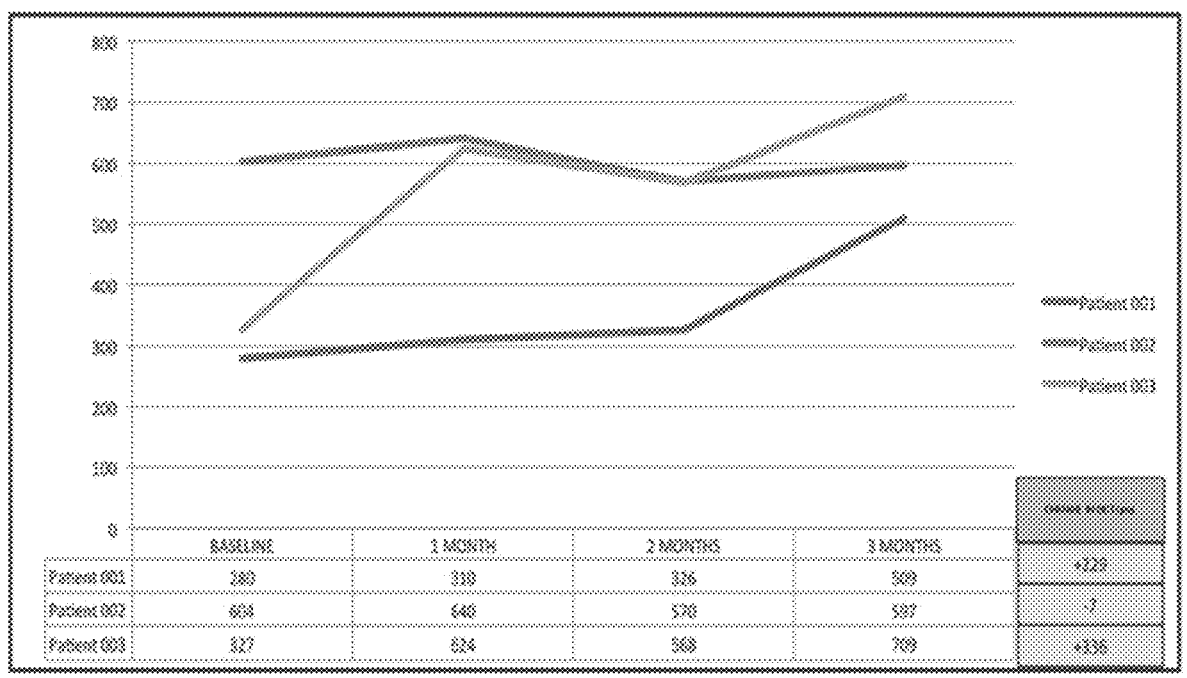
FIG. 5 shows OCT results of Central Foveal thickness of the patients contra lateral eyes over time.
Figure 6:
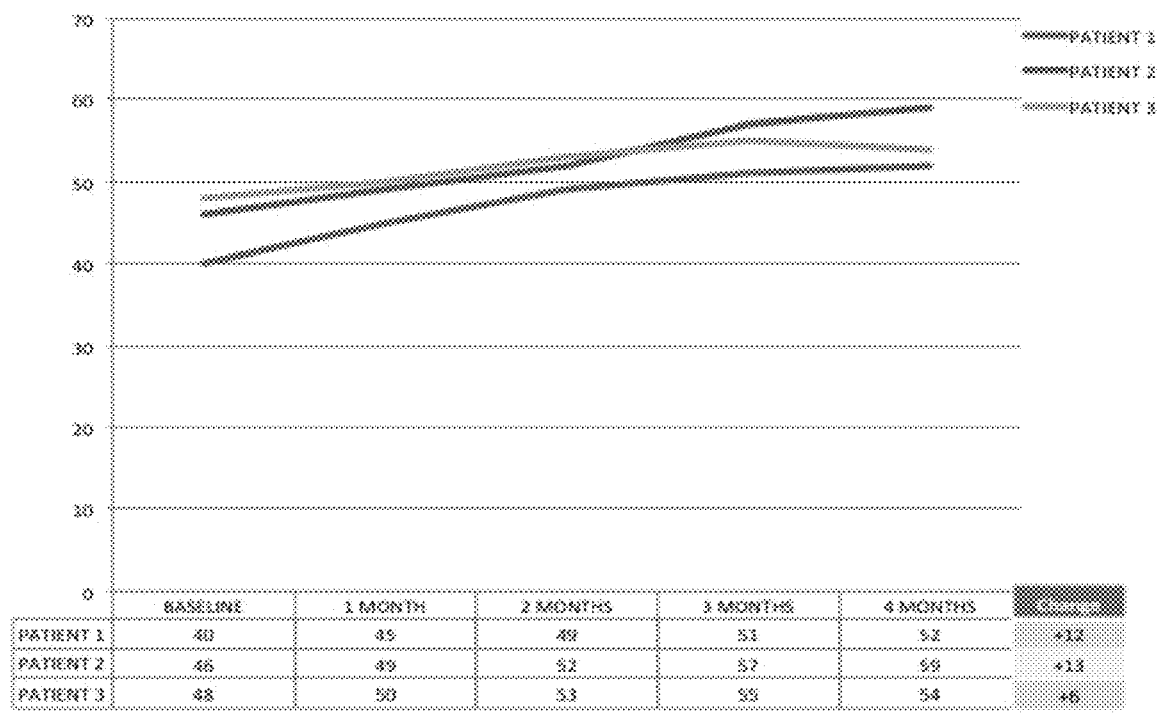
FIG. 6 shows the results of BCVA over time for the study eyes in the three patients.

The buffer solution was prepared by combining a 15 mL solution of polyoxyl 40 stearate, sodium chloride, sodium monobasic phosphate and sodium dibasic phosphate with 5 mLs of the sodium perborate solution (V=20 mL, pH 5.5). 1.45 mLs of this solution was then utilized as described directly above. The concentration of each of the excipients in the ophthalmic liposomal suspension formulation was 0.142 mg/mL (sodium phosphate dibasic); 6.7 mg/mL (sodium phosphate monobasic); 50 mg/mL (polioxil 40 stearate); 5.1 mg/mL (sodium chloride); 0.333 mg/mL (ranibizumab); 10 mgs/mL (PEG-12 GDM) and 2.8 mg/mL (sodium perborate). The pH may be adjusted with HCl or NaOH and low molecular weight amino acids or organic acids may be utilized as well. FIG. 3 shows at least two types of liposomes (Qusomes®) that are formed when the lipid is mixed with an aqueous solution (from Biozone Laboratories website).

Example 2—Diffusion Chamber Study in Rabbit Corneas

Diffusion chamber data of the liposomal formulation applied to rabbit corneas was generated using the methods described below. To summarize, samples were taken at 10, 20 and 30 minutes and at hours 1, 2, 3, 4, 5, 6 and 24. The data showed a significant rate of penetration into the aqueous humor of rabbit corneas at 34 degrees Centigrade for the liposomal ranibizumab formulation applied topically. In the liposomal formulation ranibizumab was identified starting at 3 hours and remained present up to 24 hours post administration versus 7 and 14 days previously reported in the rabbit for a non-liposomal formulation (data not shown-see Chen et al., Eye London 2011 November; 25(11): 1504-11). Experiments were conducted in glass, Valia-Chen chambers with horizontal flow. The water recirculates with a temperature of 34 degrees C. A membrane was placed between the junctions of the chambers and, in this example, rabbit corneas were used as the membrane. The receptor chamber was filed with 3.2 mLs of saline solution to simulate the content of aqueous humor in the anterior portion of the eye. The donor chamber was provided with 3 mLs of the ophthalmic formulation comprising ranibizumab and the thermodynamically stable, self-forming lipid. The diffusion chambers were constantly agitated. Samples were collected from the receptor chamber at various timepoints—400 μL samples were taken and replaced with 400 μLs of saline solution each time. The samples were taken at time points: 10 min; 20 min; 30 min; 1 hr; 2 hr; 3 hr; 4 hr; 5 hr; 6 hr and 24 hr. Ranibizumab was detected by HPLC as early as the 3$^{rd}$ hour. Lucentis® was used as a control solution for the HPLC standard. Electrophorosis was also used to evaluate the passage of the liposomal formulation through the rabbit cornea membrane and results were consistent with the HPLC data.

Example 3—Pilot Clinical Study on Patients with DME

Figure 2:
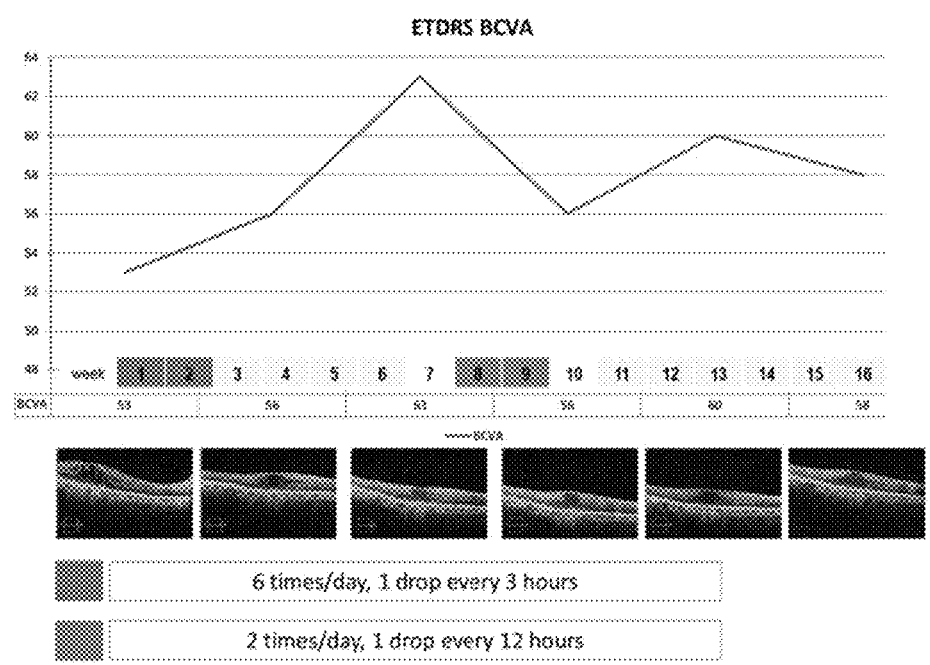
FIG. 2 shows the same clinical patient treated with a liposomal ranibizumab formulation having improved visual acuity measurements (ETDRS BCVA) over an eight week period after being dosed six drops per day for two weeks. At week eight the patient showed a decrease in VA and treatment was reinitiated at 10 weeks at a daily dose of 2 drops per day.

A patient having DME was treated six times/day with 1 drop/every three hours of the formulation on a daily basis (6x/day) for two weeks. The total dose/day of ranibizumab was 6×17 ug or 102 ug. Improvements in loss of mean central foveal thickness (CFT) and an increase in visual acuity were seen through six weeks following this two week period (See FIG. 1 and FIG. 2). At week eight an increase in retina thickness and decline in visual sharpness occurred and, at week 10, treatment was reinitiated at two drops per day (34 ug/day). At week 14 clear tendency toward improvement in OCT and BCVA was observed (see FIGS. 1 and 2). Two additional patients were also treated using the same protocol. Results of all three patients are presented in FIGS. 4-7 and show improvement in CFT and VA relative to control.

Example 4—Pilot Clinical Study on Patients with DME Using Triamcinolone Actetonide Eligible patients having DM E received a topical formulation comprising triamcinolone (TA) in a single center open label pilot study. A total of 3 eyes of 3 patients (mean age 58 years, range 53-64) with DME involving the center of the macula and best-corrected visual acuity (BCVA) in the study eye between 65 and 40 letters using ETDRS testing. Patients were instructed to apply one drop containing 133 ug (micrograms) of TA every two hours in the study eye, while they were awake (six times) during the controlled treatment period of twelve (12) weeks. The main outcome measures included primary end points at three months such as the frequency and severity of ocular and systemic adverse events and the change from baseline in the central foveal thickness (CFT), as measured by optical coherence tomography (OCT) over time. The secondary outcomes were the change from baseline BCVA score over time, proportion of patients with a >3-step progression from baseline in ETDRS retinopathy severity on fundus photographs (FP), proportion of patients with resolution of leakage on fluroescein angiography (FA) and the need of macular laser treatment over time. The TA formulation was prepared in a similar manner to the ranibizumab formulation from commercially available starting materials.

Triamcinolone+1% Liposomes Ophthalmic Suspension

Formulation 1 is a sterile, aqueous suspension. Its content is as follows:

| TA FORMULATION | |
|---|---|
| | mg/mL |
| Triamcinolone acetonide * | 2.667 |
| Hydroxypropylmethylcellulose | 3.000 |

| TA FORMULATION | |
|---|---|
| | mg/mL |
| Monobasic sodium phosphate | 10.000 |
| Dibasic sodium phosphate | 3.000 |
| Polysorbate 80 | 0.500 |
| EDTA | 0.100 |
| Sodium chloride | 2.500 |
| Benzalkonium Chloride 50% | 0.200 |
| PEG-12-GDM | 10.0000 |
| Water | 1 mL |
| NaOH or HCl to adjust pH 5.0-7.5 | Each drop of the suspension contains 133.35 μg. |

PEG-12-GDM: Liposomes; Diacylglycerol-polyethyleneglycol (PEG 12), glycerol dimyristate (GDM).
* TA is a finished product. It is TA micronized (approx. 12 mm) and free of preservatives.

Preparation Protocol of Triamcinolone+1% Liposomes Ophthalmic Suspension
1. Place 40% of the final volume of distilled water in a beaker and heat it to 70 to 80° C.
2. Add the hydroxypropylmethylcellulose and stop mixing until reaching room temperature and it becomes a clear and homogeneous mixture.
3. Autoclave it and once sterile allows it to reach room temperature while stirring.
4. Place in another beaker 40% of the final volume of distilled water. Add and mix until completely dissolved one by one the following reagents:
   a) Sodium phosphate monobasic
   b) Sodium phosphate dibasic
   c) EDTA
   d) Sodium chloride
   e) Polysorbate 80
5. In 10% of the remaining volume of water, add the benzalkonium chloride at 50% and mix until completely incorporated. Once dissolved, add this new solution to the above solution containing phosphates, EDTA, sodium chloride and Polysorbate 80. To sterilize, filter by 0.22 μm membrane.
6. Mix the sterile solution of hydroxypropylmethylcellulose with the other sterile solution containing the salts and the preservative benzalkonium chloride and mix until getting a clear homogeneous mixture.
7. Add the triamcinolone acetate to the solution with buffers and benzalkonium chloride and stir until completely incorporated.
8. Add the Liposomes to this mix and stir during 15 minutes with a magnetic stirrer to obtain a final suspension.
9. Package the suspension in special eye dropper. Each dropper bottle contained 1.5 mL of this triamcinolone ophthalmic suspension.

Results:

The use of a topical formulation comprising TA in the liposomal formulation in patients with center-involving clinically significant DME was well tolerated. Neither ocular nor systemic adverse events were reported. At month 2, the CFT of all three patients was reduced relative to baseline. Two of the three patients had a decrease in CFT of at least 100 um. At month three, all three patients showed visual acuity improvement. One of the patients gained >15 letters. The pH of this formulation is 6.24 the viscosity (cP) is 34 and the osmolarity (mOsmoL/L) is 422.

Other suitable topical triamcinolone liposomal formulations were also prepared and provided improved clinical results. The invention includes suitable non-ionic surfactants such as polysorbate. Other non-ionic surfactants can include, for example, Kolliphor HS15 (polyglycol mono- and di-esters of 12-hydroxystearic acid). One such formulation (TA-LF2) used comprises triamcinolone acetonide (2.0 mg); Kolliphor HS-15 (50 mg); PEG-12-glyceryl-dimyristate (100 mg); ethyl alcohol (14 mcL); anhydrous citric acid (0.8 mg); sodium citrate dehydrate (4.68 mg); benzalkonium chloride (0.1 mg) QS 1.0 mL water. The pH in this formulation is stable and maintained at pH 6.0. Suitable pH ranges can also be between 5.5 and 7.0. In the preferred process, the non-ionic surfactant is blended with the liposomal lipid before mixing with the active ingredient and additional excipients in the liquid formulation. The above formulation with about 10% liposomal load has improved viscosity, pH stability (pH 5.80; viscosity (cP) 70 and osmolarity (334 mOsmol/L). The formulations are stable under heat stress studies. Encapsulation percentages are enhanced with formulation 2 and the particle distribution profile is enhanced with formulation 2 as well relative to formulation 1. Clinical studies in patients with cystoid macular edema following cataract surgery showed that formulation 2 provided an excellent response in all patients tested (n=8) which had improvement in central foveal thickness measured by OCT while treatment with formulation 1 was also beneficial but required rescue treatment. In addition, formulation 2 provided a positive response in best corrected visual acuity (BCVA) measurements following cataract surgery relative to formulation 1. Treatment with formulation 2 provided an improvement in the average BCVA of more than 20 letters at week 12. The invention also relates to triamcinolone acetonide-loaded liposomes topical ophthalmic formulations for prevention of macular thickening and its associated visual outcomes after lens surgery.

The most commonly performed ophthalmologic procedure in the world is lens surgery, with approximately 20 million surgeries done in 2010 and estimated to reach 32 million by 2020. Phacoemulsification is the current preferred method wherein the lens material is softened using ultrasonic energy (emulsify) followed by extraction from the eye through irrigation and suction. Specific steps in conventional lens surgery through phacoemulsification include creating corneal incisions using a blade or keratome, manually opening the anterior capsule (capsulotomy) using a forceps or bent needle, fragmenting the lens with ultrasonic energy and chopper instruments, suction of lens material, implantation of an intraocular lens (IOL) and finally aspiration and cleanup of viscoelastic and retained lens cortical fragments. In recent years, the femtosecond laser has been utilized to perform the vital steps of corneal incision, anterior capsulotomy and lens fragmentation. A femtosecond laser is an infrared laser (1053 nm) that works by photodisruption wherein laser energy absorbed by the tissue induces rapid expansion, creating microcavitation bubbles and acoustic shock waves that cause morphological changes (1).

Femtosecond laser-assisted cataract and lens surgery (FLACS) appears to improve outcomes and safety over conventional phacoemulsification. In a recent study comparing FLACS and conventional phacoemulsification, both had comparable refractive and visual results. However, FLACS had less phacoemulsification energy, postoperative anterior chamber inflammation and corneal endothelial cell loss (1).

Therefore, current lens surgery techniques significantly reduce postoperative complications. However, pseudophakic cystoid macular edema (PCME) (macular thickening that develops after implantation of an IOL) continues to be the most common cause of decreased central visual acuity (CVA) after a successful cataract and lens surgery. The incidence of clinical PCME, defined by symptomatic vision loss, is reported between 1.17-4.04% (2), however the incidence of PCME diagnosed by optical coherence tomography (OCT) can be as high as 10.9% (3). Though, previous FLACS vs. phacoemulsification cataract surgery studies have demonstrated less increase in central macular thickness and reduced anterior chamber flare (4, 5) with FLACS, (6) PCME can still happen in FLACS. The reported prevalence of postoperative cystoid macular edema (CME) associated with FLACS is about 0.8% (7), and it could be comparable to some published rates of CME in conventional cataract phacoemulsification surgery (0.1% to 2.35%) (8, 9).

Onset of clinically significant PCME is commonly 4 to 12 weeks after surgery with its peak at 4 to 6 weeks. The typical complaint is of impaired central vision following an initial postoperative period of improvement (10). Numerous risk factors have been associated with PCME occurrence, like systemic diseases including diabetes mellitus (2, 11), YAG capsulotomy or preexisting conditions as uveitis (2, 12), use of topical prostaglandin analogs (13, 14), trauma (15), and intra-operative complications (16, 17).

The ideal treatment to prevent PCME has not been established. However, corticosteroids and topical nonsteroidal anti-inflammatory drugs (NSAIDs), either as monotherapy or in combination have proven to be useful (18-21), and are broadly used as first-line drugs (22). For instance, in a retrospective study for the prevention of PCME (defined as new or worsening of anatomic macular edema or thickening demonstrated by OCT), the postoperative rates of macular edema in patients receiving prednisolone acetate 1% and dexamethasone sodium phosphate 0.1% were 4.0% and 4.1% respectively (20).

Recently, a topical triamcinolone acetonide-loaded liposomes formulation (TA-LF) was used to efficaciously deliver triamcinolone (TA) into vitreous and retina of rabbits (23) and its therapeutic efficiency was verified in patients with refractory PCME (24). Liposomes-based eye drops have been proposed as a drug delivery system into the posterior segment of the eye, and they have the potential to deliver drugs like TA in therapeutic concentrations to the vitreous cavity and retina (23). Liposomes (LPs) are particles composed of an aqueous core and delimited by a membrane-like lipid bilayer that works as carriers for water-soluble, lipid-soluble and amphiphilic drugs (25-28). LPs are non-toxic, low antigenic, easily metabolized and biodegradable (29) and they have been employed to improve drug transport and bioavailability in ocular tissues (30, 31).

The compositions of the present invention (a formulation) comprise a combination of triamcinolone acetonide as the active pharmaceutical ingredient, polyethylene glycol (PEG-12) glyceryl dimyristate as structural constituent of liposomes, ethyl alcohol as organic solvent for liposomes generation, kolliphor HS 15 as penetration enhancer, citric acid anhydrous and sodium citrate dehydrate as buffers, benzalkonium chloride as preservative, and grade 2 purified water as inorganic solvent. Other suitable formulations are disclosed in U.S. Pat. Pub. 2015/0224055 which is hereby incorporated by reference in its entirety.

The formulations of the present invention are useful for prevention of macular thickening and its associated visual outcomes after lens surgery, such as; visual acuity and contrast sensitivity.

The present invention relates to topical ophthalmic formulations suitable for the treatment of conditions which occur in association with lens surgeries. In particular, the inventors have discovered a use of a topical ophthalmic liposomal formulation developed for the treatment of posterior segment diseases of the eye. The present invention relates to the further discovery that this formulation is particularly useful for the treatment of patients that have undergone cataract surgeries.

The compositions of the present invention contain a pharmaceutically effective amount of triamcinolone acetonide (TA). The concentration of TA in liposomes formulations ranges from 0.01 to 2.00% (w/v). TA is a known synthetic corticosteroid with an empirical formula of $C_{24}H_{31}FO_6$ and a molecular weight of 434.50 Da. TA has a powerful anti-inflammatory activity (7.5 times more potent than cortisone) (32). Polyethylene glycol (PEG-12) glyceryl dimyristate is used as structural constituent of liposomes in a concentration of 5-15% (w/v) and ethyl alcohol is used as organic solvent for liposomes generation in a concentration of 0.7 to 2.1% (v/v).

Besides, the liposomes formulation contain polyethylene glycol (15)-hydroxystearate or KolliphorHS 15 from 2.5-7.5% (w/v), as a potent non-ionic solubilizer and emulsifying agent, with low toxicity proposed to act as a permeability enhancer. KolliphorHS 15 promotes drug transport across cell membranes (increasing the endocytosis rate) and stimulates drug translocation through the paracellular route (affects actin organization on the cell cytoskeleton with the subsequent tight junction opening) (33).

Additionally, the aqueous compositions of the present invention optionally comprise more excipients selected from the group consisting of buffering agents, pH-adjusting agents, and preservatives. Citric acid anhydrous (0.04-0.16%) and sodium citrate dehydrate (0.23-0.69%) are used as buffers, whereas benzalkonium chloride (0.001-0.015%) as preservative. All of these compounds in units of % w/v. The pH can range from about 5 to about 7.5.

Ingredient concentrations are presented in units of % weight/volume (% w/v) or % volume/volume (% v/v).

The compositions of the present invention may be prepared by conventional methods of preparing pharmaceutical suspension compositions. According to the preferred method, the drug (triamcinolone acetonide) is first added to a lipid mixture containing polyethylene glycol (PEG-12) glyceryl dimyristate and ethyl alcohol. An aqueous mixture having grade 2 purified water, polyethylene glycol (15)-hydroxystearate (KolliphorHS 15), citric acid anhydrous, sodium citrate dehydrate and benzalkonium chloride was commingled in a flask and set aside for compounding. The water mixture is gently added to the lipid mixture to obtain the final formulation.

Example 5

The formulations shown below are representative of the compositions of the present invention. The formulation used in the clinical studies below is formulation 2 (TA-LF or TA-LF2) as shown in Table 1. Example 4 used a different formulation (formulation 1).

TABLE 1

Triamcinolone acetonide-loaded liposomes topical ophthalmic formulation (TA-LF)

|  | (w or v) | (%) |
| --- | --- | --- |
| Triamcinolone acetonide | 2.0 mg | 0.2 w/v |
| Kolliphor HS 15 | 50 mg | 5 w/v |
| PEG-12 glyceryl dimyristate | 100 mg | 10 w/v |
| Ethyl alcohol | 14 mL | 1.40% v/v |

TABLE 1-continued

Triamcinolone acetonide-loaded liposomes topical ophthalmic formulation (TA-LF)

|  | (w or v) | (%) |
| --- | --- | --- |
| Citricacidanhydrous | 0.8 mg | 0.08 w/v |
| Sodiumcitratedihydrate | 4.675 mg | 0.4675 w/v |
| Benzalkoniumchloride | 0.1 mg | 0.01 w/v |
| Grade 2 purifiedwater | Q.S. 1.0 ml | NA NA |

NA; not applicable
v; volume,
w, weight

The formulations shown in Table 1 were prepared and subjected to a physicochemical characterization. pH of TA-FL was analyzed by a pH meter in triplicate at room temperature. Osmolarity was measured by a vapor pressure osmometer and performed in triplicate at 33° C. (the ocular surface temperature) (34). Viscosity was measured also in triplicate at 33° C. Viscosity was measured using a thermostatically controlled rheometer when the steady state was reached with shear rates increasing from 0 to 1000 s−1. Particle size of the TA-LFs was analyzed by means of Dynamic Light Scattering and zeta potential ($\zeta$) was calculated by measuring the velocity of the particles using Laser Doppler Velocimetry at 25° C. (Zetasizer Nano ZS, Malvern Instruments, Malvern, UK). The Z-average (mean particle diameter) and polydispersity index (PDI) were calculated from the particle size distribution.

TABLE 2

Physicochemical properties of TA-LF.

| Formulation | pH | Viscosity (cP) | Osmolarity (mOsm/l) | Z-average (nm) | PDI (nm) |
| --- | --- | --- | --- | --- | --- |
| TA-LF | 5.8 | 70 | 334 | 187.8 | 0.369 | pH = hidrogenion potential,
cP = centipoise,
PDI = polydispersity index
Values represent the average of three measures Posteriorly, TA-LF from example 5 was evaluated in an in vitro diffusion assay. Diffusion chambers and rabbit corneas were used to conduct diffusion experiments (Chemotaxis Chambers BW200S, NeuroProbe, Gaithersburg, Md., USA). Rabbit corneas from New Zealand white rabbits were used for this experiment. The central corneal tissue was located between the top and bottom compartments of the diffusion chambers to act as a TA diffusion barrier. The top compartment was filled with 180 μl of balanced salt solution (BSS) while the bottom compartment was filled with 200 μl of TA-LFs (TA-LF1 to TA-LF4). To avoid evaporation, the diffusion chambers were located into a 37° C. humidity camera. The TA concentration analysis of solutions obtained from the top compartment at 2, 4, 6 and 8 hours (h) after starting the diffusion assay, was performed by high performance liquid chromatography (HPLC). HPLC was performed using a Varian 920 LC (Aligent Technologies, Santa Clara, Calif., USA) with a Zorbax Eclipse Plus C18, 4.6× 100 mm and 3.5-μm column (Agilent, Santa Clara, Calif., USA) at 30° C. The samples (20 μl) were eluted from the column in a mobile phase comprised of water:methanol (30:70) at a flow rate of 1 ml/min. Detection was performed at 254 nm. Retention time and detection limit were 6.8 min and 0.004 mg/ml respectively. The TA standard curve was linear from 0.004 to 0.100 mg/ml (correlative >0.99). In vitreous, concentrations of TA were determined for the recovery and intra- and inter-day reproducibility (35).

Result from the in vitro diffusion assay is exposed in table 3.

TABLE 3

TA concentration in the top solution of the diffusion chamber across time

| Time (hours) | TA Concentration (µg/mL) |
|---|---|
| 2 | 0.22 |
| 3 | 0.35 |
| 4 | 0.5 |
| 5 | 0.65 |
| 6 | 0.8 |
| 7 | 0.95 |
| 8 | 1.1 |

Values represent the average of three measures.

We observed that TA-LF (formulation 2) presented the best diffusion performance, reaching the highest TA concentrations after 8 hours of follow up.

After in vitro assays and in vivo diffusion analysis of and tolerability assessment of TA-LF was performed in rabbits. For diffusion analysis, concentrations of TA were determined by HPLC in ocular tissues from New Zealand white rabbits after multiple doses of TA-LF2. For tolerability assessment, eye examination of study animals was performed after topical administration of TA-LF. The protocol for animals was the following. Rabbits were randomly distributed into four groups. One-drop TA-LF2 solution (50 µl) was applied to one eye every two hours 6 times during 14 days. Five rabbits were sacrificed after starting the instillation of TA-LF2 at 12 hours, 1, 7 and 14 days. Before tissue collecting, an eye examination was performed under anesthesia (intramuscular injection of ketamine hydrochloride 30 mg/kg and chlorpromazine hydrochloride 15 mg/kg). This evaluation included slit-lamp biomicroscopy, fluorescein staining, funduscopy with direct ophthalmoscope, and intraocular pressure (IOP) measurement (iCare Tonometer i350, Vantaa, Finland). Additionally, ocular irritability test was evaluated according to pharmacopeia of Estados Unidos Mexicanos. A positive irritant reaction is considered when more than one rabbit presented: cornel ulceration revealed by fluorescein staining, corneal opacity, iris or conjunctival inflammation and dilatation of conjunctival vessels especially around the cornea. After enucleation, conjunctiva, cornea, retina, 150 µl of aqueous humor and 200 µl of vitreous were collected. The solid tissues were washed in PBS. Then, tissues were homogenized with 0.3 ml of acetonitrile (Sigma-Aldrich, Mexico). Posteriorly, each sample was centrifuged at 15,294×g for 5 min. The supernatants were evaporated to add 100 µl of methanol. Another centrifugation was performed and 20 µl of the resultant supernatants were used for analysis of TA concentration by HPLC, performed as previously described.

The concentrations of TA in retina and vitreous reached the highest peak at 12 hours (252.1±90.00 ng/g and 32.6±10.27 ng/g respectively) to subsequently decline to 24.0±11.72 ng/g and 19.5±13.14 ng/g respectively at 14 days of follow up. TA concentration vs time in different ocular tissues are presented in FIG. 5 and Table 4.

TABLE 4

Ocular tissues concentration of TA after topical administration of TA-LF in rabbit eyes.
Triamcinoloneacetonideconcentration (ng/g)

| Time (days) | Conjunctiva | Cornea | Lens | Retina | Aqueous | Vitreous |
|---|---|---|---|---|---|---|
| 0.5 | 1886.3 ± 398.95 | 2156.1 ± 1055.41 | 83.3 ± 30.49 | 252.1 ± 90.00 | 9.9 ± 1.95 | 32.6 ± 10.27 |
| 1 | 1524.8 ± 356.04 | 657.5 ± 260.37 | 62.2 ± 18.54 | 196.9 ± 133.10 | 9.8 ± 2.12 | 18.6 ± 7.07 |
| 7 | 359.3 ± 166.54 | 132.5 ± 78.37 | 52.3 ± 37.42 | 57.7 ± 20.92 | 8.1 ± 2.71 | 20.7 ± 11.35 |
| 14 | 52.3 ± 27.82 | 92.3 ± 42.13 | 5.2 ± 3.38 | 24 ± 11.72 | 2.8 ± 0.13 | 19.5 ± 13.14 |

Values represent the average ± standard deviation of the mean of four samples

Compartmental and non-compartmental model were used to determine pharmacokinetics of TA-loaded liposomes in ocular tissues. Linear-trapezoidal method was employed to evaluate the area under the curve (AUC). The half-life ($t_{1/2}$) was calculated by linear regression of the concentration at different times. Pharmacokinetic parameters are shown in table 5.

$C_{max}$ was 2156.07±1055.41 ng/g in cornea, 1886.33±398.95 ng/g in conjunctiva, 9.9±1.95 ng/g in aqueous humor, 83.3±30.49 ng/g in lens, 32.6±10.27 ng/g in vitreous and 252.10±90.00 ng/g in retina.

TABLE 5

Pharmacokinetics parameters in ocular tissues after topical administration of TA-FL.

| Parameter | Conjunctiva | Cornea | Aqueous | Lens | Vitreous | Retina |
|---|---|---|---|---|---|---|
| $k_e$ (d$^{-1}$) | 0.263 | 0.26 | — | — | 0.79 | 0.26 |
| $T_{1/2}$ (d) | 2.64 | 2.66 | 0.23 | 0.09 | 0.87 | 3.62 |
| $C_{max}$ (ng/g) | 1886.33 | 2156.075 | 9.94 | 83.328 | 32.6 | 252.1 |
| $C_{min}$ (ng/g) | 52.26 | 92.348 | 2.795 | 5.183 | 18.613 | 24 |
| $k_{12}$ (d$^{-1}$) | — | 2.365 | — | — | 13.48 | 0.383 |
| $k_{21}$ (d$^{-1}$) | — | 0.045 | — | — | 0.018 | 0.478 |

TABLE 5-continued

Pharmacokinetics parameters in ocular tissues after topical administration of TA-FL.

| Parameter | Conjunctiva | Cornea | Aqueous | Lens | Vitreous | Retina |
|---|---|---|---|---|---|---|
| $ABC0^{-t}$ (ng * g/d) | 7,945.35 | 3,860.50 | 96.75 | 610.052 | 271.378 | 1,159.40 |
| $ABC0^{\infty}$ (ng * g/d) | 8,144.32 | 3,933.12 | — | — | 296.054 | 1,251.69 |

$k_e$ = elimination rate constant;
d = day;
$T_{1/2}$ = elimination half-life $C_{max}$ = observed maximum concentration;
$C_{min}$ = observed minimum concentration;
$k_{12}$ = rate of transfer from central to peripheral compartment;
$k_{21}$ = rate of transfer from peripheral to central compartment;
$AUC0^{-t}$ = area under the curve until the last measurable;
$AUC0^{\infty}$ = area under the curve from 0 to infinity.

Related to tolerability assessment; no increase in intraocular pressure was observed in any of the study subjects (normal intraocular pressure in this species is 12-28 mmHg). Staining with fluorescein sodium and bengal rose showed superficial punctate keratitis in the first 6 hours after instillation of the formulation. This condition was resolved in all cases in the examination at 12 hours after the administration of the formulation. Therefore, according to pharmacopeia of EstadosUnidosMexicanos, ocular irritability test was satisfactory, and TA-LF2 is considered nonirritant.

Finally, therapeutic activity of TA-LF (formulation 2) was proved in humans. In three clinical trials (phase 0, phase 1, and phase II) the evaluation of tolerability, safety and efficacy of a topical TA-LF was performed.

Clinical Trial Phase 0

This study was performed to report tolerability, safety and efficacy of a topical triamcinolone acetonide-loaded liposomes formulation (TA-LF2) to target the macular area in patients with refractory pseudophakic cystoid macular edema (PCME). For tolerability, safety and efficacy evaluation, 12 eyes of 12 patients with refractory PCME were exposed to one drop of TA-LF (TA at 0.2%) every two hours for 90 days or until best-corrected visual acuity (BCVA) was achieved. Intraocular pressure (IOP), slit lamp examination and central foveal thickness (CFT) were analyzed at every visit. Patients with refractory PCME under TA-LF therapy showed a significant improvement of BVCA and CFT without significant IOP modification (P=0.94). On average CFT decreases 184±113.82 μm and BCVA improves 22.33±4.32 letters (P<0.0005). BCVA was achieved at 10.58±7.20 weeks (range, 2-18). TA-LF was well tolerated in all cases. No ocular surface abnormalities nor adverse events were recorded. Results of the intervention are summarized in table 6. In conclusion of the phase 0 study: TA-LF was well tolerated and improved BCVA and CFT on patients with refractory PCME. The results of this clinical trial were recently published (24).

TABLE 6

Demographics and Clinical Characteristics of patients with PCME treated with TA-LF.

| | | | | Baseline | | | |
|---|---|---|---|---|---|---|---|
| Patient | Gender | Age (years) | Study eye | CFT (μm) | BCVA (ETDRS letters) | IOP (mmHg) | Vitrectomy |
| 1 | F | 63 | OD | 545 | 52 | 17 | Yes |
| 2 | F | 76 | OD | 580 | 46 | 15 | Yes |
| 3 | M | 59 | OS | 461 | 43 | 12 | Yes |
| 4 | F | 58 | OS | 369 | 49 | 15 | Yes |
| 5 | F | 62 | OS | 605 | 53 | 13 | No |
| 6 | F | 74 | OD | 487 | 50 | 12 | Yes |
| 7 | F | 78 | OS | 600 | 54 | 14 | No |
| 8 | M | 59 | OS | 415 | 47 | 14 | No |
| 9 | M | 64 | OS | 354 | 53 | 17 | No |
| 10 | F | 66 | OD | 666 | 52 | 11 | No |
| 11 | M | 60 | OD | 596 | 50 | 14 | No |
| 12 | M | 64 | OS | 360 | 45 | 12 | No |
| | M: 5 (41.66%) F: 7 (58.33%) | 68.08 ± 12.16 | OD: 5 (41.66%) OS: 7 (58.33%) | 503.17 ± 110 | 49.5 ± 3.55 | 13.83 ± 1.95 | Yes: 5 (41.66%) No: 7 (58.33%) |

| | TA-LF therapy results | | | | | | | |
|---|---|---|---|---|---|---|---|---|
| Patient | CFT at the time of BCVA (μm) | CFT change (μm) | BCVA (ETDRS letters) | BCVA change (ETDRS letters) | Weeks to BCVA | *IOP (mmHg) | IOP change (mmHg) | AEs |
| 1 | 330 | −215 | 70 | 18 | 2 | 12 | 5 | No |
| 2 | 333 | −247 | 73 | 27 | 7 | 11 | 4 | No |
| 3 | 329 | −132 | 67 | 24 | 17 | 11 | 1 | No |
| 4 | 328 | −41 | 80 | 31 | 2 | 17 | −2 | No |
| 5 | 352 | −253 | 73 | 20 | 13 | 14 | −1 | No |

TABLE 6-continued

Demographics and Clinical Characteristics of patients with PCME treated with TA-LF.

| | | | | | | | | | |
|---|---|---|---|---|---|---|---|---|---|
| 6 | 288 | −199 | 80 | 30 | 2 | 11 | | 1 | No |
| 7 | 352 | −248 | 58 | 4 | 17 | 16 | | −2 | No |
| 8 | 391 | −24 | 73 | 26 | 22 | 13 | | 1 | No |
| 9 | 262 | −92 | 70 | 17 | 18 | 13 | | 4 | No |
| 10 | 260 | −406 | 80 | 28 | 13 | 18 | | −7 | No |
| 11 | 316 | −280 | 58 | 8 | 11 | 18 | | −4 | No |
| 12 | 289 | −71 | 80 | 35 | 3 | 13 | | −1 | No |
| | 319.17 ± 38.68† | −184 ± 113.82 | 71.83 ± 7.88† | 22.33 ± 4.32 | 10.58 ± 7.20 | 13.92 ± 2.68‡ | | −0.08 ± 3.50 | Yes: 0 (0.00%) No: 12 (100%) |

F; female,
M; male,
OD; right eye,
OS; left eye,
CFT; central foveal thickness,
BCVA; best corrected visual acuity,
ETDRS; Early Treatment Diabetic Retinopathy Study,
IOP; intraocular pressure,
TA-LF; Triamcinolone acetonide loaded liposomes formulation,
AEs; adverse events
*IOP; IOP at 20 weeks of follow-up,
†statistically significant differences from baseline values ($P < 0.0005$),
‡no statistically significant differences from baseline values ($P > 0.05$).

Clinical Trial Phase 1

This study was performed to report tolerability, safety and efficacy of a topical triamcinolone acetonide-loaded liposomes formulation (TA-LF2) in healthy subjects, with no ocular nor systemic disease. They received the TA-LF and were instructed to apply one drop every two hours in the right eye, while awake (six times), for 2 weeks. Demographic and baseline clinical exams were collected on day 14 to 1 before starting the administration of TA-LF. Retinal optical coherence tomography (OCT) was performed at baseline (to confirm no CME by OCT) and every week until the end of the follow-up. BCVA using the Early Treatment of Diabetic Retinopathy Study (ETDRS) chart at 4 m, IOP, slit lamp evaluation of the eye surface with fluorescein 2% staining and posterior segment findings were recorded on every visit. Subjects were withdrawn from the study if they presented any evidence of poor tolerability (any adverse event related to the use of the topical formulation). Tolerability was assessed through collection and summary of ocular and non-ocular adverse events (AEs), serious AEs (SAEs), ocular assessments and vital signs, whether volunteered by the patient, discovered by study site personnel during questioning, or other means. Subjects were withdrawn if they presented any evidence of poor tolerability or any adverse event, such as corneal ulcers, corneal opacities, epithelial defects, anterior chamber inflammation (cell/flare) and conjunctival and/or epiescleral injection related to the use of this topical formulation. AEs were assigned standard codes terms for the event based upon the MedDRA Coding dictionary version 18.1.

TA-LF2 was well tolerated in healthy subjects. Twenty right eyes of 20 healthy subjects (38.45±9.06 years old, female; 45%, male; 55%) without evidence of systemic or eye disease were enrolled to evaluate tolerability of the TA-LF2. These subjects were instructed to apply one drop of TA-LF every two hours in the right eye, while they were awake (six times), during 2 weeks. Demographic and baseline clinical characteristics of these subjects are summarized in Table 7. In data analysis, no AEs were reported. OCT showed no significant change in CFT as compared with baseline (CFT change of 0.85±0.29 □m). BCVA did not have a significant change in all 20 patients (average change of −0.01±0.16 ETDRS letters). No ocular surface abnormalities were recorded during the follow up period. None of the patients showed significant increase in IOP during the treatment period. None of the patients were excluded from the study due AEs. Clinical characteristics after TA-LF2 treatment in healthy subjects are summarized in Table 7.

TABLE 7

Demographics and Clinical Characteristics of healthy subjects treated with TA-LF.

| | | | | Baseline Characteristics | | | Week 12 (TA-LF) | | | | | |
|---|---|---|---|---|---|---|---|---|---|---|---|---|
| | | | | | | | | | BCVA | | | |
| Patient | Gender | Age (years) | Study eye | CFT (μm) | BCVA (ETDRS letters) | IOP (mmHg) | CFT (μm) | CFT chamge (mm) | BCVA (ETDRS letters) | change (ETDRS letters) | IOP (mmHg) | IOP change (mmHg) | AEs |
| 1 | F | 46 | OD | 260 | 81 | 13 | 262 | 2 | 81 | 0 | 16 | 3 | No |
| 2 | M | 45 | OD | 241 | 80 | 14 | 245 | 4 | 79 | −1 | 13 | −1 | No |
| 3 | F | 58 | OD | 247 | 82 | 15 | 247 | 0 | 81 | −1 | 16 | 1 | No |
| 4 | M | 47 | OD | 262 | 80 | 15 | 262 | 0 | 80 | 0 | 12 | −3 | No |
| 5 | M | 37 | OD | 254 | 84 | 12 | 254 | 0 | 84 | 0 | 14 | 2 | No |
| 6 | M | 32 | OD | 250 | 85 | 15 | 255 | 5 | 85 | 0 | 16 | 1 | No |

TABLE 7-continued

Demographics and Clinical Characteristics of healthy subjects treated with TA-LF.

| | | | | Baseline Characteristics | | | Week 12 (TA-LF) | | | | | |
| | | | | | | | | | BCVA | | | |
| Patient | Gender | Age (years) | Study eye | CFT (μm) | BCVA (ETDRS letters) | IOP (mmHg) | CFT (μm) | CFT change (mm) | BCVA (ETDRS letters) | change (ETDRS letters) | IOP (mmHg) | IOP change (mmHg) | AEs |
|---|---|---|---|---|---|---|---|---|---|---|---|---|---|
| 7 | F | 50 | OD | 243 | 82 | 16 | 241 | −2 | 82 | 0 | 16 | 0 | No |
| 8 | F | 35 | OD | 265 | 85 | 17 | 270 | 5 | 85 | 0 | 17 | 0 | No |
| 9 | M | 28 | OD | 259 | 85 | 13 | 256 | −3 | 85 | 0 | 15 | 2 | No |
| 10 | M | 31 | OD | 240 | 85 | 13 | 243 | 3 | 84 | −1 | 12 | −1 | No |
| 11 | F | 33 | OD | 259 | 85 | 10 | 260 | 1 | 85 | 0 | 11 | 1 | No |
| 12 | F | 36 | OD | 248 | 83 | 14 | 248 | 0 | 84 | 1 | 15 | 1 | No |
| 13 | M | 39 | OD | 249 | 82 | 16 | 249 | 0 | 82 | 0 | 14 | −2 | No |
| 14 | F | 50 | OD | 257 | 80 | 17 | 257 | 0 | 80 | 0 | 15 | −2 | No |
| 15 | M | 48 | OD | 247 | 84 | 14 | 248 | 1 | 84 | 0 | 14 | 0 | No |
| 16 | F | 24 | OD | 249 | 85 | 14 | 250 | 1 | 85 | 0 | 11 | −3 | No |
| 17 | M | 27 | OD | 245 | 85 | 13 | 245 | 0 | 85 | 0 | 12 | −1 | No |
| 18 | F | 33 | OD | 242 | 84 | 13 | 242 | 0 | 85 | 1 | 15 | 2 | No |
| 19 | M | 35 | OD | 257 | 83 | 12 | 257 | 0 | 82 | −1 | 12 | 0 | No |
| 20 | M | 35 | OD | 248 | 82 | 15 | 248 | 0 | 82 | 0 | 18 | 3 | No |
| | M: 11 (55%) F: 9 (45%) | 38.45 ± 9.06 | OD: 20 (100%) OS: 0 (0.00%) | 251.1 ± 7.49 | 83.1 ± 1.86 | 14.05 ± 1.76 | 251.9 ± 7.79‡ | 0.85 ± 0.29 | 83 ± 2.02‡ | −0.01 ± 0.16 | 14.2 ± 2.04‡ | 0.15 ± 0.28 | Yes: 0 (0.00%) No: 12 (100%) |

F; female,
M; male,
OD; right eye;
BCVA; best corrected visual acuity,
ETDRS; Early Treatment Diabetic Retinopathy Study,
IOP; intraocular pressure,
CFT; central foveal thickness,
AEs; adverse events,
TA-LF; Triamcinolone acetonide loaded liposomes formulation,
†statistically significant differences from baseline values ($P < 0.05$),
‡no statistically significant differences from baseline values ($P > 0.05$).

Clinical Trial Phase II

The aim of this assay is to explore tolerability, safety and efficacy of a topical triamcinolone acetonide-loaded liposomes formulation (TA-LF; formulation 2 or TA-LF2) to prevent Clinical significant pseudophakic cystoid macular edema (CSME) after femtosecond laser-assisted cataract surgery (FLACS). Fifty-five eyes of 32 patients underwent FLACS were enrolled. Twenty-seven eyes were assigned to TA group whereas twenty-eight eyes were assigned to TA-LF group. In TA group, eyes were exposed to a conventional topical formulation of triamcinolone acetonide 0.1% for 21 days postoperatively whereas patients in the TA-LF group received a liposomal formulation containing 2 mg/ml of TA (0.2%). A follow up consisting of slit lamp examination, visual acuity, contrast sensitivity, central foveal thickness (CFT) and total macular volume (TMV) (both measured by retinal optical coherence tomography) was performed. Study visits were scheduled at 1 day, 6 and 12 weeks after surgery. Related to tolerability and safety outcomes, TA-LF was well tolerated during the study period. Neither ocular (increased intra-ocular pressure, ocular surface abnormalities) nor systemic adverse events were reported. None of the patients required IOP lowering drugs. None of the patients showed signs of irritation or surface problems due to the study formulation application until the end of the study. On the other hand, only TA-LF group shown a significant improvement in contrast sensitivity (basal value; 1.087±0.339 vs week 12; 1.266±0.147) and visual acuity from the preoperative measures (basal value; 0.252±0.248 vs week 12; 0.005±0.136). Table 8 summarized the analysis of variables within groups.

TABLE 8

Differences within groups in visual acuity, contrast sensitivity, macular thickness and total macular volume.

| | | Basal | 6 w | 12 w | P value |
|---|---|---|---|---|---|
| Visual acuity (logMar) | TA | 0.054 ± 0.148 | 0.072 ± 0.189 | 0.077 ± 0.195 | 0.9779 |
| | TA-LF | 0.252 ± 0.248 | 0.03 ± 0.142 | 0.005 ± 0.136 | <0.0001 |
| Contrast sensitivity (1/contrast) | TA | 1.214 ± 0.219 | 1.194 ± 0.173 | 1.229 ± 0.178 | 0.513 |
| | TA-LF | 1.087 ± 0.339 | 1.217 ± 0.191 | 1.266 ± 0.147 | 0.0346 |
| CFT (μm) | TA | 258.33 ± 32.50 | 275.37 ± 43.22 | 275.38 ± 47.26 | 0.0143 |
| | TA-LF | 256.21 ± 15.16 | 266.42 ± 16.06 | 265.92 ± 18.55 | <0.0001 |
| TMV (mm$^3$) | TA | 10.14 ± 0.70 | 10.41 ± 0.58 | 10.52 ± 0.69 | 0.031 |
| | TA-LF | 10.08 ± 0.71 | 10.55 ± 0.52 | 10.50 ± 0.52 | <0.0001 |

TABLE 8-continued

Differences within groups in visual acuity, contrast sensitivity, macular thickness and total macular volume.

|  |  | Basal | 6 w | 12 w | P value |
|---|---|---|---|---|---|
| IOP (mmHg) | TA | 15.11 ± 3.25 | 12.88 ± 3.02 | 13.52 ± 2.50 | 0.0193 |
|  | TA-LF | 15.71 ± 2.20 | 12.89 ± 2.69 | 13.50 ± 1.93 | 0.0193 |

CFT; central foveal thickness, IOP; intraocular pressure, logMar: logarithm of the minimal angle of resolution; TA; Triamcinolone acetonide group, TA-LF; liposomal formulation containing 2 mg/ml of TA group, TMV; total macular volume, w; week.

Remarkably, CFT and TMV correlate significantly with contrast sensitivity only in TA-LF group. The $r^2$ for CFT and contrast sensitivity was 0.1675 (P=0.0306), whereas the $r^2$ for TMV and contrast sensitivity was 0.1675 (P=0.0055) (Table 9).

TABLE 9

Correlation between CFT and TMV with visual acuity and contrast sensitivity in TA and TALF groups.

|  |  | Visual acuity (logMar) | | Contrast sensitivity (1/contrast) | |
|---|---|---|---|---|---|
|  |  | $r^2$ | P value | $r^2$ | P value |
| TA | CFT | 0.04249 | 0.3023 | 0.01382 | 0.854 |
|  | TMV | 0.00008 | 0.9629 | 0.01236 | 0.5809 |
| TA-LF | CFT | 0.1036 | 0.0948 | 0.1675 | 0.0306 |
|  | TMV | 0.06301 | 0.1976 | 0.2605 | 0.0055 |

CFT; central foveal thickness, logMar: logarithm of the minimal angle of resolution; TA; Triamcinolone acetonide group, TA-LF; liposomal formulation containing 2 mg/ml of TA group, TMV; total macular volume, w; week.

Lastly, TA-LF shown the best preventive action for CSME. The incidences of cystoid macular edema (CME) and clinical significant CME (CSME) in TA group at 6 weeks were 3.7% and 22.2% respectively, whereas the incidences of these findings in the TA-LF group were in contrast 3.7% and 0% (Table 10).

The odds of developing CSME were significantly higher in the TA group than in TA-LF group (OR, 9.44; 95% Cl, 1.76-50.66; P=0.027). All patients with CSME in the TA group required rescue treatment (a topical combination of prednisolone 1% 4 times daily and nepafenac 0.1% 3 times daily for 4 weeks was considered when patients developed CSME during the course of the study).

In conclusion of this study, TA-loaded liposomal formulation is effective for the prevention of CSME associated with FLACS and it seems that its therapeutic activity could be superior to the activity of conventional topical steroids formulation. The use of TA-LF was related to better visual outcomes like visual acuity and contrast sensitivity.

TABLE 10

Incidence of CME and CSME and Odds Ratio values.

| Parameter | TA Incidence n/N (%) | TA-LF Incidence n/N (%) | OR (95% CI)* | P value |
|---|---|---|---|---|
| CME within 6 w | 1/27 (3.7) | 1/28 (3.5) | 1.038 (0.0617-17.48) | 0.97 |
| CME within 12 w | 1/21 (4.7) | 1/28 (3.5) | 1.33 (0.078-22.57) | 0.84 |
| CSME within 6 w | 6/27 (22.2) | 0/28 (0) | 9.44 (1.76-50.66) | 0.027 |
| CSME within 12 w | 0/21 (0) | 0/28 (0) | 1.325 (0.025-69.52) | 0.88 |

CI; confidence interval, CME; cystoid macular edema, CSME; clinically significant macular edema, OR; Odds Ratio, TA; Triamcinolone acetonide group, TA-LF; liposomal formulation containing 2 mg/ml of TA group.
Odds of developing CME and CSME in the TA group are presented.

Figure 8:
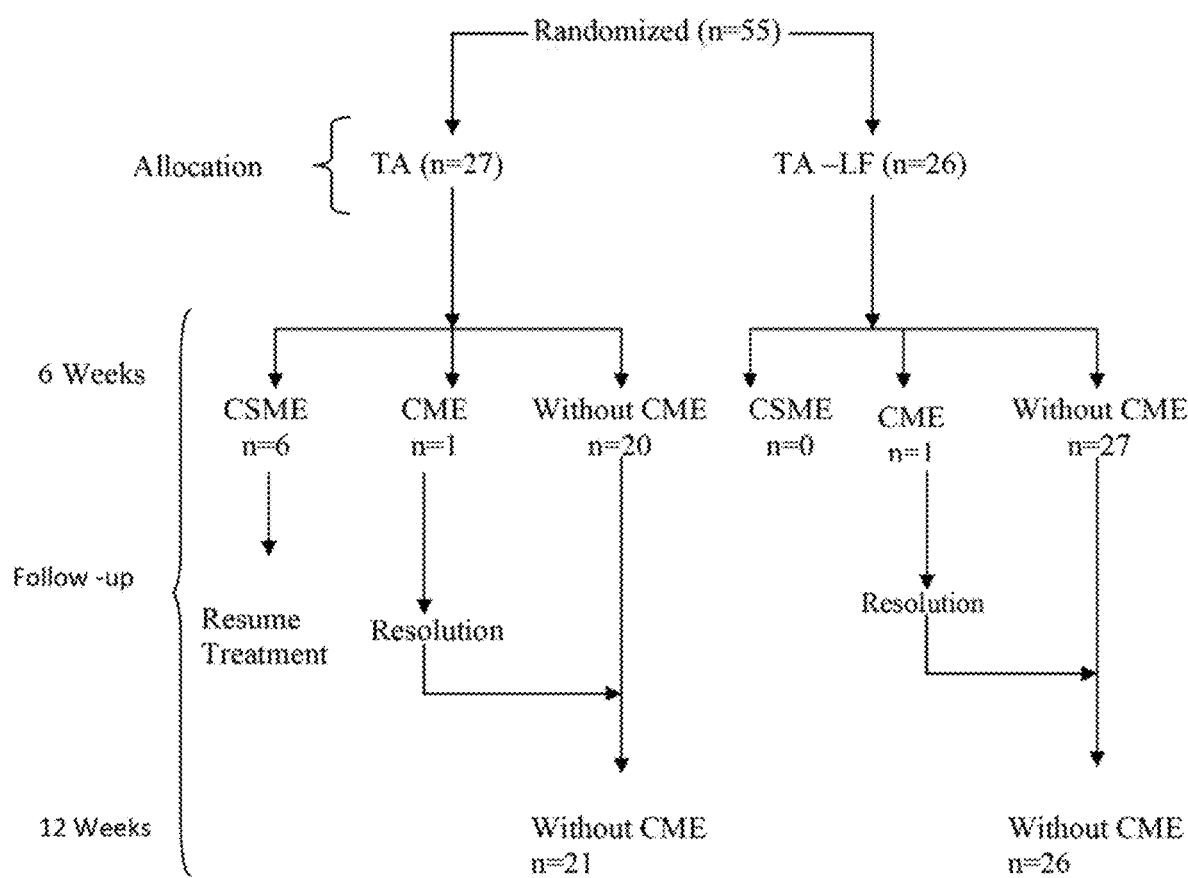
FIG. 8 shows a flow diagram representing the number of eyes randomized and analyzed, and shows TA-LF (formulation 2) treatment provided significant results in preventing CSME (clinically significant macular edema). CSME was present in 6/27 cases of treatment with a non-liposomal commercial triamcinolone product versus 0/27 cases in the treatment arm with TA-LF.

FIG. 8 represents the number of eyes randomized and analyzed. TA-LF showed excellent results preventing CSME (clinically significant macular edema). CSME (clinically significant macular edema) was present in 6/27 cases of triamcinolone (commercial product) vs. 0/27 cases with TA-LF. For CME (Cystoid macular edema) both groups have 1 patient each. Liposomal formulation containing 2 mg/ml of TA group.

Figure 9:
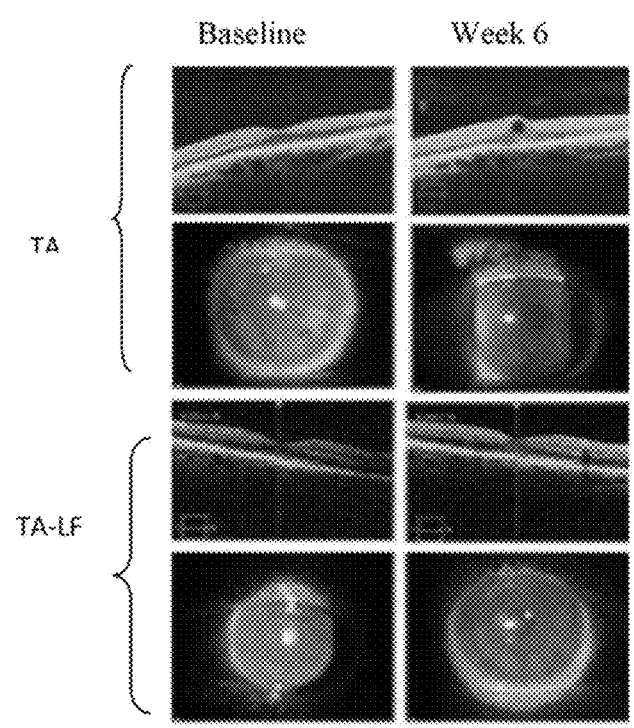
FIG. 9 shows Baseline and post-operative images of fluorescein eye surface staining and OCT images in the TA and TA-LF groups. The tomographic images in the TA Group correspond to one of the six cases of CSME whereas the tomographic images in the TA-LF group showed only one case of CSME

FIG. 9 represents Baseline and post-operative images of fluorescein eye surface staining and OCT images in the TA and TA-LF groups are presented. The tomographic images in TA group correspond to one of the six cases of CSME, whereas the tomographic images in the TA-LF group correspond to the only case of CME. As shown in the photographs, non-ocular surface adverse events were revealed by fluorescein stain at 6 weeks of follow-up in any group.

While the claimed invention has been described in detail and with reference to specific embodiments thereof, it will be apparent to one of ordinary skill in the art that various changes and modifications can be made to the claimed invention without departing from the spirit and scope thereof. Thus, for example, those skilled in the art will recognize or be able to ascertain using no more than routine experimentation, numerous embodiments of the claimed invention which may not have been expressly described. Such embodiments are within the scope of the invention.

REFERENCES

1. Roskoski Jr, Sunitinib: A VEGF and PDGF receptor protein kinase and angiogenesis inhibitor. BBRC, 2007.
2. Fong D, Diabetic Retinopathy. Diabetes Care, 2004.
3. Bhagat N, Diabetic Macular Edema: Pathogenesis and Treatment. Survey of Ophthalmology 2009.
4. Meyer C, Current Treatment Approaches in Diabetic Macular Edema, Ophthalmologica, 2007.
5. Chen Y, Selection and analysis of an optimized Anti-VEGF antibody: Crystal structure of an affinity-matured Fab in complex with antigen, JMB, 1999.

6. Presta L, Humanization of an Anti-vascular endothelial growth factor monoclonal antibody for the therapy of solid tumors and other disorders.
7. ETDRSR, Photocoagulation for macular Edema, Report 1, 1985.
8. Ang R E T, Quinto M M S, Cruz E M, Rivera M C R, Martinez G H A. Comparison of clinical outcomes between femtosecond laser-assisted versus conventional phacoemulsification. Eye Vis (Lond). 2018; 5:8.
9. Chu C J, Johnston R L, Buscombe C, Sallam A B, Mohamed Q, Yang Y C, et al. Risk Factors and Incidence of Macular Edema after Cataract Surgery: A Database Study of 81984 Eyes. Ophthalmology. 2016; 123(2):316-23.
10. Perente I, Utine C A, Ozturker C, Cakir M, Kaya V, Eren H, et al. Evaluation of macular changes after uncomplicated phacoemulsification surgery by optical coherence tomography. Curr Eye Res. 2007; 32(3):241-7.
11. Ecsedy M, Mihaltz K, Kovacs I, Takacs A, Filkorn T, Nagy Z Z. Effect of femtosecond laser cataract surgery on the macula. J Refract Surg. 2011; 27(10):717-22.
12. Nagy Z Z, Ecsedy M, Kovacs I, Takacs A, Tatrai E, Somfai G M, et al. Macular morphology assessed by optical coherence tomography image segmentation after femtosecond laser-assisted and standard cataract surgery. J Cataract Refract Surg. 2012; 38(6):941-6.
13. Abell R G, Allen P L, Vote B J. Anterior chamber flare after femtosecond laser-assisted cataract surgery. J Cataract Refract Surg. 2013; 39(9):1321-6.
14. Ewe S Y, Oakley C L, Abell R G, Allen P L, Vote B J. Cystoid macular edema after femtosecond laser-assisted versus phacoemulsification cataract surgery. J Cataract Refract Surg. 2015; 41(11):2373-8.
15. Henderson B A, Kim J Y, Ament C S, Ferrufino-Ponce Z K, Grabowska A, Cremers S L. Clinical pseudophakic cystoid macular edema. Risk factors for development and duration after treatment. J Cataract Refract Surg. 2007; 33(9):1550-8.
16. Zur D, Loewenstein A. Postsurgical Cystoid Macular Edema. Dev Ophthalmol. 2017; 58:178-90.
17. Coscas G, Cunha-Vaz J, Soubrane G. Macular Edema: Definition and Basic Concepts. Dev Ophthalmol. 2017; 58:1-10.
18. Schmier J K, Halpern M T, Covert D W, Matthews G P. Evaluation of costs for cystoid macular edema among patients after cataract surgery. Retina. 2007; 27(5):621-8.
19. Belair M L, Kim S J, Thome J E, Dunn J P, Kedhar S R, Brown D M, et al. Incidence of cystoid macular edema after cataract surgery in patients with and without uveitis using optical coherence tomography. Am J Ophthalmol. 2009; 148(1):128-35 e2.
20. Yeh P C, Ramanathan S. Latanoprost and clinically significant cystoid macular edema after uneventful phacoemulsification with intraocular lens implantation. J Cataract Refract Surg. 2002; 28(10):1814-8.
21. Panteleontidis V, Detorakis E T, Pallikaris I G, Tsilimbaris M K. Latanoprost-Dependent Cystoid Macular Edema Following Uncomplicated Cataract Surgery in Pseudoexfoliative Eyes. Ophthalmic Surg Lasers imaging. 2010:1-5.
22. Rossetti L, Autelitano A. Cystoid macular edema following cataract surgery. Curr Opin Ophthalmol. 2000; 11(1):65-72.
23. Nikica G, Ljerka H P, Jelena P, Metez-Soldo K, Mladen B. Cystoid macular edema in anterior chamber lens implantation following posterior capsule rupture. Doc Ophthalmol. 1992; 81(3):309-15.
24. Ah-Fat F G, Sharma M K, Majid M A, Yang Y C. Vitreous loss during conversion from conventional extracapsular cataract extraction to phacoemulsification. J Cataract Refract Surg. 1998; 24(6):801-5.
25. Chinchurreta Capote A M, Lorenzo Soto M, Rivas Ruiz F, Caso Pelaez E, Garcia Vazquez A, Group O, et al. Comparative study of the efficacy and safety of bromfenac, nepafenac and diclofenac sodium for the prevention of cystoid macular edema after phacoemulsification. Int J Ophthalmol. 2018; 11(7): 1210-6.
26. El Gharbawy S A, Darwish E A, Abu Eleinen K G, Osman M H. Efficacy of addition of nepafenac 0.1% to steroid eye drops in prevention of post-phaco macular edema in high-risk eyes. Eur J Ophthalmol. 2018: 1120672118799626.
27. Baartman B J, Gans R, Goshe J. Prednisolone versus dexamethasone for prevention of pseudophakic cystoid macular edema. Can J Ophthalmol. 2018; 53(2): 131-4.
28. Ylinen P, Holmstrom E, Laine 1, Lindholm J M, Tuuminen R. Anti-inflammatory medication following cataract surgery: a randomized trial between preservative-free dexamethasone, diclofenac and their combination. Acta Ophthalmol. 2018; 96(5):486-93.
29. Guo S, Patel S, Baumrind B, Johnson K, Levinsohn D, Marcus E, et al. Management of pseudophakic cystoid macular edema. Sunr Ophthalmol. 2015; 60(2):123-37.
30. Altamirano-Vallejo J C, Navarro-Partida J, Gonzalez-De la Rosa A, Hsiao J H, Olguin-Gutierrez J S, Gonzalez-Villegas A C, et al. Characterization and Pharmacokinetics of Triamcinolone Acetonide-Loaded Liposomes Topical Formulations for Vitreoretinal Drug Delivery. J Ocul Pharmacol Ther. 2018; 34(5):416-25.
31. Gonzalez-De la Rosa A, Navarro-Partida J, Altamirano-Vallejo J C, Hernandez-Gamez A G, Garcia-Banuelos J J, Armendariz-Borunda J, et al. Novel Triamcinolone Acetonide-Loaded Liposomes Topical Formulation for the Treatment of Cystoid Macular Edema After Cataract Surgery: A Pilot Study. J Ocul Pharmacol Ther. 2019; 35(2):106-15.
32. Klibanov A L, Maruyama K, Torchilin V P, Huang L. Amphipathic polyethyleneglycols effectively prolong the circulation time of liposomes. FEBS Lett. 1990; 268(1): 235-7.
33. Lopez-Berestein G, Mehta R, Hopfer R, Mehta K, Hersh E M, Juliano R. Effects of sterols on the therapeutic efficacy of liposomal amphotericin B in murine candidiasis. Cancer Drug Deliv. 1983; 1(1):37-42.
34. Oku N, Nojima S, Inoue K. Selective release of non-electrolytes from liposomes upon perturbation of bilayers by temperature change or polyene antibiotics. Biochim Biophys Acta. 1980; 595(2):277-90.
35. Allen T M, Cullis P R. Drug delivery systems: entering the mainstream. Science. 2004; 303(5665): 1818-22.
36. van Rooijen N, van Nieuwmegen R. Liposomes in immunology: multilamellar phosphatidylcholine liposomes as a simple, biodegradable and harmless adjuvant without any immunogenic activity of its own. Immunol Commun. 1980; 9(3):243-56.
37. Di Tommaso C, Bourges J L, Valamanesh F, Trubitsyn G, Torriglia A, Jeanny J C, et al. Novel micelle carriers for cyclosporin A topical ocular delivery: in vivo cornea penetration, ocular distribution and efficacy studies. Eur J Pharm Biopharm. 2012; 81(2):257-64.
38. Hathout R M, Mansour S, Mortada N D, Guinedi A S. Liposomes as an ocular delivery system for acetazolamide: in vitro and in vivo studies. AAPS PharmSciTech. 2007; 8(1):1.

39. Mansoor S, Kuppermann B D, Kenney M C. Intraocular sustained-release delivery systems for triamcinolone acetonide. Pharm Res. 2009; 26(4):770-84.
40. Shubber S, Vllasaliu D, Rauch C, Jordan F, Ilium L, Stolnik S. Mechanism of mucosal permeability enhancement of CriticalSorb® (Solutol® HS15) investigated in vitro in cell cultures. Pharm Res. 2015; 32(2):516-27.
41. Purslow C, Wolffsohn J S. Ocular surface temperature: a review. Eye Contact Lens. 2005; 31(3):117-23.
42. Shabir G A. Validation of high-performance liquid chromatography methods for pharmaceutical analysis. Understanding the differences and similarities between validation requirements of the U S Food and Drug Administration, the US Pharmacopeia and the International Conference on Harmonization. J Chromatogr A. 2003; 987(1-2):57-66.

What is claimed is:

1. A method of treating a VEGF-related posterior-segment disease or condition comprising administering a pharmaceutically effective amount of a combination of (1) an intravitreal formulation of ranibizumab by intravitreal injection and (2) a topical ophthalmic formulation comprising an anti-VEGF antibody and a thermodynamically stable, self-forming liposome to the surface of the eye of a patient in need of treatment thereof wherein the topical ophthalmic formulation comprises
   a) an anti-VEGF antibody selected from ranibizumab bevacizumab
   b) the self-forming liposome
   c) a non-ionic surfactant and
   d) a buffer; and
   wherein the dosing frequency of said intravitreal injection is reduced due to administration of said combination.

2. The method according to claim 1, wherein the anti-VEGF antibody is selected from ranibizumab.

3. The method according to claim 1, wherein a lipid that forms the thermodynamically stable, self-forming liposome is fluid at 25° C. and comprises a PEG chain having a molecular weight of between about 300 and about 5,000 Daltons and is self-forming in an aqueous solution at both 20° C. and 37° C. and the lipid is selected from PEG-12-GDM.

4. The method according to claim 3, wherein the topical formulation is a topical ophthalmic formulation is administered at a dosage of about 34-102 µg/day.

5. The method according to claim 3, wherein the lipid is selected from the group consisting of PEG-12 GDM or PEG-12 GDO.

6. The method according to claim 1, wherein the VEGF-related disease or condition is selected from a neoplastic or non-neoplastic disease or condition.

7. The method according to claim 6, wherein the non-neoplastic disease is selected from the group consisting of rheumatoid arthritis, psoriasis, atherosclerosis, diabetic arid other proliferative retinopathies including retinopathy of prematurity, retrolental fibroplasias. neovascular glaucoma, age-related macular degeneration, diabetic macular edema and other forms of macular edema, thyroid hyperplasias including Grave's disease, corneal and other tissue transplantation, chronic inflammation, lung inflammation, nephritic syndrome, preclampsia, ascites, pericardia effusions and pleural effusion.

8. The method according to claim 7, wherein the disease or condition is selected from age-related macular degeneration, diabetic macular edema or corneal neovascularization and the topical formulation comprises,
   a) ranibizumab,
   b) Polyethyleneglycol (PEG-12) glyceryl dimyristate
   c) Ethyl alcohol
   d) Polyethylene glycol (15)-hydroxystearate
   e) Citric acid anhydrous
   f) Sodium citrate dehydrate
   g) Benzalkonium chloride,
   h) purified water.

* * * * *